(12) United States Patent
Wilson et al.

(10) Patent No.: US 9,200,328 B1
(45) Date of Patent: Dec. 1, 2015

(54) METHODS AND KITS FOR DIAGNOSING THE PROGNOSIS OF CANCER PATIENTS

(71) Applicant: NEW YORK UNIVERSITY, New York, NY (US)

(72) Inventors: Elaine Lynette Wilson, New York, NY (US); Liliana Ossowski, Forest Hills, NY (US); Phillip Ross Smith, New York, NY (US)

(73) Assignee: NEW YORK UNIVERSITY, New York, NY (US)

( * ) Notice: Subject to any disclaimer, the term of this patent is extended or adjusted under 35 U.S.C. 154(b) by 0 days.

(21) Appl. No.: 13/830,325

(22) Filed: Mar. 14, 2013

Related U.S. Application Data

(60) Provisional application No. 61/610,802, filed on Mar. 14, 2012.

(51) Int. Cl.
*C12Q 1/68* (2006.01)
*G01N 33/68* (2006.01)

(52) U.S. Cl.
CPC .......... *C12Q 1/6886* (2013.01); *G01N 33/6893* (2013.01)

(58) Field of Classification Search
None
See application file for complete search history.

(56) References Cited

U.S. PATENT DOCUMENTS

| | | |
|---|---|---|
| 5,474,796 A | 12/1995 | Brennan |
| 2009/0162329 A1 * | 6/2009 | Anversa et al. ............... 424/93.7 |

FOREIGN PATENT DOCUMENTS

WO   WO 2011068839 A1 *   6/2011   ............... C12Q 1/68

OTHER PUBLICATIONS

SuperArray / RT[2] PCR Array product sheet, SABiosicences/Qiagen, published Feb. 2012, obtained from http://www.sabiosciences.com/manuels/PP_GEF_RT2Profiler_0212_web.pdf.*
Affymetrix Data Sheet: GeneChip Human Genome Arrays, p. 1-4, 2003-2004.

* cited by examiner

*Primary Examiner* — Tracy Vivlemore
*Assistant Examiner* — Karen S Weiler
(74) *Attorney, Agent, or Firm* — Browdy and Neimark, PLLC

(57) ABSTRACT

The prognosis of a cancer patient can be determined by analyzing the modulation of expression of specified genes in the tumor tissue. Genes uniquely up-regulated in adult stem cells that can reconstitute the tissue of the tumor are analyzed for up-regulation in the patient's tumor. Up-regulation of a plurality of such genes in the tumor is an indication of good prognosis. Genes uniquely up-regulated in fetal stem cells are analyzed for up-regulation in the patient's tumor. Up-regulation of a plurality of such genes in the tumor are an indication of a poor prognosis. Specific genes are disclosed, the modulation of which, in a patient's prostate cancer tumor, will serve as an indication of prognosis. Patients with a good prognosis are subjected to watchful waiting. Patients with a poor prognosis are aggressively treated. Kits are provided containing a set of affinity reagents that specifically detect expression of the various genes.

31 Claims, 17 Drawing Sheets
(17 of 17 Drawing Sheet(s) Filed in Color)

METHODS AND KITS FOR DIAGNOSING THE PROGNOSIS OF CANCER PATIENTS

This invention was made with government support under Grant No. 1 US1 RR029893 awarded by National Center for Research Resources, National Institutes of Health, DHHS, Grant No. RO1 CA132641 from the National Cancer Institute, National Institutes of Health, DHHS, and Grant UL1 TR000038 from the National Center for Advancing Translational Sciences of the National Institutes of Health. The government has certain rights in the invention.

FIELD OF THE INVENTION

The present invention relates generally to methods for diagnosing the prognosis of cancer patients, and more particularly to the analysis of uniquely up-regulated adult stem cell genes and uniquely up-regulated fetal stem cell genes in the tumor cells of the patient. The presence in the patient's tumor cells of a significant number of uniquely up-regulated adult stem cell genes (adult stem cells have a signature of quiescence), in stem cells having a high capacity to reconstitute the normal tissue from which the tumor originates, is an indicator of good prognosis. The up-regulation in the tumor cells of genes that are uniquely up-regulated in fetal stem cells (which have a signature of proliferation) of such tissue is an indicator of poor prognosis. The invention further relates to specific genes, the modulation of which in prostate tumor cells will be indicative of prognosis.

BACKGROUND OF THE DISCLOSURE

Prostate cancer is a heterogeneous disease, ranging from asymptomatic to a rapidly fatal metastatic malignancy in men. It is the most commonly diagnosed cancer in men in the US, with approximately 240,000 newly diagnosed patients and over 30,000 cancer deaths each year. Progress in treating human prostate cancer has been hampered by the finding that histologically similar cancers can exhibit widely variant clinical behavior. For example, in some men, the disease progresses slowly with a prolonged natural history while in others, disease progression can be rapid so that local therapy is ineffective. The uncertainty regarding appropriate clinical management of prostate cancer in many patients is related to the fact that similar tumor phenotypes can harbor diverse molecular and genetic changes that can affect prostate cancer development and disease progression.

A variety of clinical models or nomograms have been developed to aid clinicians with pre-treatment risk assessment. For example, since 1988, the routine use of serum prostate-specific antigen (PSA) testing in men at risk for prostate cancer has led to more favorable disease characteristics at presentation (mainly more localized disease) and more effective treatment. Several investigators have used these clinical parameters to stratify patients into risk groups (low, intermediate, high) and to predict clinical outcomes (Nomograms). Despite these useful parameters, approximately 20-30% of patients with low to intermediate-risk prostate cancer fail standard treatment as evidenced by a rising serum PSA following definitive therapy. A better understanding of the molecular abnormalities that define tumors from patients who are at high risk for relapse is needed to help stratify patients into biologically defined groups with similar risk factors.

Three well-defined predictors of disease extent and outcome following treatment are known in newly diagnosed patients. These factors are (1) clinical tumor stage (T1-T4) by digital rectal examination, (2) Gleason score of the diagnostic biopsy specimen and (3) serum PSA levels. However, each of these factors alone has not proven definitive in predicting disease extent and outcome for an individual patient. Clinical staging by digital rectal examination may underestimate the presence of extracapsular disease extension in 30-50% of patients. Although, Gleason score on biopsies may be helpful in predicting pathologic stage and outcome following treatment at either end of the spectrum (i.e., Gleason 2-4 or Gleason 8-10 tumors), it is less helpful for the majority of patients who present with "intermediate" Gleason 5-7 disease. As risk assessment methods for patients newly diagnosed with prostate cancer continue to evolve, newer tools, such as genetic or molecular determinants are expected to be able to better predict the behavior of an individual tumor.

Surgical treatment is usually reserved for prostate cancer patients in good general health with tumor confined to the prostate gland (Stage I and Stage II). However, a fraction of these patients will fail the treatment as judged by chemical failure (elevation of PSA level) or development of metastasis (commonly in lymph nodes and bone). Urgent need also exists for methods that can stratify patients with clinically-low risk disease into active surveillance vs. definitive therapy. Currently, a significant proportion of patients face uncertainty with respect to their decision to undergo surgery or to choose active surveillance as well as their prognosis after surgery. Existing methods for assessing clinical risk include the various pathological (e.g., tumor stage), histological (e.g., Gleason's score), molecular biomarkers (e.g., PSA), or more complex methods which combine those markers in a nomogram (e.g. Kattan, et al., "Postoperative nomogram for disease recurrence after radical prostatectomy for prostate cancer," *J Clin Oncol*, 17:1499-1507 (1999)). However, using these methods for future risk assessment is unreliable in ~20 to 30% of prostate cancer patients with low or intermediate stage disease. Routine PSA testing has increased the pool of patients with early disease and, with this, the need for more reliable stratification. The ability to identify, or predict, a post-surgery patient as likely to encounter PSA failure, recurrence of the prostate cancer, and/or development of metastasis, would provide multiple benefits to the patient.

Currently, no single diagnostic test is capable of predicting with high certainty clinical progression of the disease. Although detection of prostate cancer is routinely achieved with physical examination and/or clinical tests such as serum PSA, a definitive diagnosis of prostate cancer requires confirmation by biopsy and histopathological evaluation.

In patients with clinically extreme disease (very early or very advanced), currently available prognostic approaches predict more reliably the probability of disease-free survival. Previous studies correlated patient survival time with the extent and spread of the prostatic carcinoma. For example, studies have shown that when the cancer is confined to the prostate gland, median survival in excess of five years can be anticipated. Patients with locally advanced cancer have a much poorer prognosis. Other factors affecting the prognosis of patients with prostate cancer that are useful in making therapeutic decisions include histologic grade of the tumor, patient's age, other medical illnesses, and PSA levels. However, such factors, as mentioned above, are of more limited value in a large proportion of intermediate stage tumors.

Information on any condition of a particular patient and a patient's response to therapeutic or nutritional agents has become an important issue in clinical medicine not only from the aspect of efficiency of medical practice for the health care industry but for improved outcomes and benefits for patients.

The clinical course of prostate cancer can be unpredictable and the prognostic significance of the current diagnostic measures remains limited.

It is now recognized that prostate cancer exhibits altered gene expression changes in hundreds of genes, many of which genes directly influence outcome. Bibikova, M., et al., "Expression signatures that correlated with Gleason score and relapse in prostate cancer," *Genomics*, 89(6):666-72 (2007); Henshall, S. M., et al., "Survival analysis of genome-wide gene expression profiles of prostate cancers identifies new prognostic targets of disease relapse," *Cancer Res*, 63(14):4196-203 (2003); Quinn, D. I., et al., "Molecular markers of prostate cancer outcome," *Eur J Cancer*, 41(6): 858-87 (2005); Henshall, S. M., et al., "Zinc-alpha2-glycoprotein expression as a predictor of metastatic prostate cancer following radical prostatectomy,"*J Natl Cancer Inst*, 98(19): 1420-4 (2006); Stephenson, R. A, et al., "Metastatic model for human prostate cancer using orthotopic implantation in nude mice," *Journal of the National Cancer Inst*, 84: 951-7 (1992); Stuart, R. O., et al., "In silico dissection of cell-type-associated patterns of gene expression in prostate cancer," *Proc Natl Acad Sci USA*, 101(2):615-20 (2004); Richardson, A M., et al., "Global expression analysis of prostate cancer-associated stroma and epithelia," *Diagn Mol Pathol*, 16(4): 189-97 (2007). See also U.S. patent publications US2010-0009581, US2011-0153534, US2011-0136683, US2011-0251987; US2009-0298082; US2010-0047787; US2011-0236903; US2011-0230361; US2010-0137164; and US2012-0028264. However a recent consensus statement by a panel of prostate SPORE leaders (the Inter-SPORE Prostate Biomarkers Study and NBN Pilot group) has tersely summarized that few or none have proven reliable enough to advance to clinical use (prostatenbnpilot.nci.nih.gov/aboutpilot_ipbs.asp).

Thus, a need exists for large-scale discovery, validation, and clinical application of mRNA biosignatures of disease and for methods of genomic analysis in patients with established clinical prostate cancer to predict disease outcomes, thereby aiding in the diagnosis, in the management of therapy, as well as in the ability to predict the survival time of patients with prostate cancer. The present invention satisfies this need and provides additional advantages.

SUMMARY OF THE INVENTION

One aspect of the present invention is a method for predicting the prognosis of a cancer patient having a tissue specific tumor. Examples of such tissue specific tumors are prostate, breast, brain and hematopoietic tumors. First, one must know which genes are uniquely up-regulated in adult stem cells that have a high capacity to reconstitute the tissue in which the tissue-specific tumor is found, as compared to the expression of genes in adult fully differentiated cells of that specific tissue. The patient's tumor cells are analyzed for up-regulated expression of such genes that are uniquely up-regulated in the adult stem cells. If a plurality of genes that are uniquely up-regulated in adult stem cell genes are also up-regulated in the tumor cells, as compared to normal cells of the same tissue or tumor cells of the same tissue in a plurality of other patients, then a good prognosis is determined and a less aggressive treatment regimen is indicated.

Similarly, one must know which genes are uniquely up-regulated in fetal stem cells that have a high capacity to reconstitute the tissue in which the tissue-specific tumor is found, as compared to the expression of genes in the adult fully differentiated cells of that specific tissue. To determine if a poor prognosis is indicated, and thus more aggressive treatment, one determines if a plurality of genes that are uniquely up-regulated in fetal stem cell genes are also up-regulated in the tumor cells, as compared to normal cells of the same tissue or tumor cells of the same tissue in a plurality of other patients. Furthermore, down-regulation of the genes found to be uniquely up-regulated in adult stem cells is also likely to be an indication of poor prognosis, thereby indicating that more aggressive treatment would be warranted.

Analysis of the patient's tumor cells involves a molecular assay that measures expression level(s) of one or more genes, gene subsets, microRNAs, or one or more microRNAs in combination with one or more genes or gene subsets, from a biological sample obtained from the cancer patient, coupled with an analysis of the measured expression levels to provide information concerning the prognosis. The biological sample may be obtained using standard methods, including surgery, biopsy, or obtaining a body fluid and may comprise tumor tissue or cancer cells. Expression levels can also be assayed by a protein-based assay to determine the levels of protein produced by such genes, such as by immunodetection using antibodies specific for such proteins.

The present invention also provides a method for determining the prognosis for a patient with prostate cancer, with the aggressiveness of treatment being indicated accordingly. The levels of expression of one or more of the following genes in the prostate tumor cells of the patient are determined: JUNB, KLF4, FOXH1, FOS, CLDN4, PADI4, B3GNT5, CDC7, PANK1, UNG, CBR3, and ATF3. This determination may be done on excised tumor cells obtained as a result of surgery, in which case the prognosis will be for recurrence. Or the determination may be done with a biopsy, or the like, without surgery, in which case the prognosis will be for a good or bad outcome, such as a disease-specific death or disease progression. This may also be used to predict the necessity of removing the primary tumor from that patient. The expression level of one or more of these genes is determined and compared to the expression level of the same gene(s) in normal prostate tissue or in prostate tumor samples from a plurality of other patients. The levels of expression in prostate tumor samples from other patients may, for example, be obtained from databases showing a wide array of gene expression in prostate tumor surgical samples. Up-regulation of JUNB, KLF4, FOXH1, FOS, CLDN4, PADI4, B3GNT5, CDC7, CBR3, and ATF3 and down-regulation of PANK1 and UNG indicate a good prognosis. Thus, alteration in the expression of 1, 2, 3, 4, 5, 6, 7, 8, 9, 10, 11 or all 12 of these genes in the manner described above, establishes a good prognosis, i.e., the likelihood of a good outcome. Any number of these genes may be analyzed as long as the desired number of genes has the specified expression modulation (meaning up- or down-regulation). Up-regulation of both of JUNB and KLF4 are particularly determinative of a good prognosis. An indication of good prognosis in patients that have not undergone surgery would indicate an active surveillance regimen, rather than aggressive therapy, such as surgery. An indication of good prognosis in patients that have already undergone surgery would also indicate an active surveillance regimen, rather than more aggressive post-surgery therapy.

Conversely, it has been demonstrated that knockdown of JUNB and/or KLF4 genes in prostate tumor cells vastly increases their invasivity and likelihood of metastasis. Accordingly, the present invention is further directed to determining a poor prognosis, with a likelihood that the tumor will be particularly prone to invasiveness and metastasis, by looking for the expression levels of the above-described good prognosis genes in a direction opposite to that which provides the good prognosis. In other words, if expression levels of two or more of JUNB, KLF4, FOXH1, FOS, CLDN4, PADI4, B3GNT5, CDC7, CBR3, and ATF3 are down-regulated and/or PANK1 and UNG are up-regulated, this would be an indicator of the tumor being prone to invasivity and metastasis. Preferably, two of the genes tested in this regard are JUNB and KLF4. If such a particularly virulent tumor is determined, aggressive steps to remove, reduce or otherwise treat the tumor should be taken.

Also provided here is a method for determining a poor prognosis in a patient with prostate cancer, again, either before or after surgery. Expression levels of one or more of the following genes in the prostate tumor cells of the patient are determined: ACAT1, ANLN, ARHGDIG, ASPN, BNC1, BRCA1, BUB1B, C13ORF3, C6ORF105, C8ORF34, CASC5, CCNA2, CDKN3, CENPF, CENPI, CHPF, CIT, DEGS1, DIRAS2, DLGAP5, DNAH8, DUSP26, E2F8, EFNA3, ELFN2, EME1, EPHA6, ESPL1, EVPL, FAP, FKBP10, FOLH1, HBE1, HCG_1774568, IGF2BP3, INCENP, IRS4, IVL, KIF11, KIF4A, KIF4B, KRT1, LOC654342, MELK, MKI67, MLF1IP, NCAPG, NCAPG2, NFS1, NOX4, NUSAP1, ONECUT2, PRC1, PRR3, PSAPL1, PSAT1, PTPRR, RACGAP1, RAMP2, RELN, RP11-49G10.8, SCGN, SLC2A13, SLC31A2, SLC35F1, SLC6A10P, SMC2, SYT9, TAS2R10, TEX101, THSD1, TPX2, TSSC1, TTK, UBE2C, UNC13C, USP9Y, UTS2D, WNT4, WT1, ZFP41, AASDHPPT, ACIN1, ACSL5, ACTN1, AHNAK, ANKRA2, ANKRD36, ANO5, ANXA1, ASCC3, B4GALT1, BACE2, BTBD3, C10ORF26, C18ORF25, CASP4, CD44, CDK10, CEP110, CHD3, COG4, CTR9, CWF19L2, CYP1B1, CYP27A1, DDHD2, DDX6, DENND2D, DPP4, DYM, EED, EFCAB4B, EPC1, ERAP1, FAM122C, FAM13B, FAM178A, FAS, FBXO21, GALNS, GBP2, GSTM1, HLA-A, HYDIN, IFI16, IL6ST, KIAA0174, KIAA1009, KIAA1328, KLHL2, KRT14, LEPR, LNPEP, LOC652614, LRRK1, MAN2A1, MAP3K1, MBD1, MT1X, MTSS1, MTUS1, NAPG, NRBP2, OGN, PCNX, PDK4, PHACTR2, PHLPP, PI15, PITPNC1, PLAA, PLEKHF2, PRKD3, PSEN1, PSMB8, PSPC1, RAB11FIP2, RBBP7, RBBP8, RBM41, RGS2, RGS22, RND3, RNPC3, RPRD1A, SATB1, SCN7A, SDCCAG10, SETBP1, SH3RF2, SLC15A2, SPG7, SQRDL, SRD5A2, ST6GAL1, SYNCRIP, TNFRSF10D, TNRC6A, TRIM22, ZADH2, ZBTB20, ZNF259, ZNF334, and ZNF532. The expression level of one or more of these genes is compared to the expression level of the same gene(s) in normal prostate tissue or in prostate tumor samples from a plurality of other patients. Up-regulation of a plurality of ACAT1, ANLN, ARHGDIG, ASPN, BNC1, BRCA1, BUB1B, C13ORF3, C6ORF105, C8ORF34, CASC5, CCNA2, CDKN3, CENPF, CENPI, CHPF, CIT, DEGS1, DIRAS2, DLGAP5, DNAH8, DUSP26, E2F8, EFNA3, ELFN2, EME1, EPHA6, ESPL1, EVPL, FAP, FKBP10, FOLH1, HBE1, HCG_1774568, IGF2BP3, INCENP, IRS4, IVL, KIF11, KIF4A, KIF4B, KRT1, LOC654342, MELK, MKI67, MLF1IP, NCAPG, NCAPG2, NFS1, NOX4, NUSAP1, ONECUT2, PRC1, PRR3, PSAPL1, PSAT1, PTPRR, RACGAP1, RAMP2, RELN, RP11-49G10.8, SCGN, SLC2A13, SLC31A2, SLC35F1, SLC6A10P, SMC2, SYT9, TAS2R10, TEX101, THSD1, TPX2, TSSC1, TTK, UBE2C, UNC13C, USP9Y, UTS2D, WNT4, WT1 and ZFP41 and down-regulation of a plurality of AASDHPPT, ACIN1, ACSL5, ACTN1, AHNAK, ANKRA2, ANKRD36, ANO5, ANXA1, ASCC3, B4GALT1, BACE2, BTBD3, C10ORF26, C18ORF25, CASP4, CD44, CDK10, CEP110, CHD3, COG4, CTR9, CWF19L2, CYP1B1, CYP27A1, DDHD2, DDX6, DENND2D, DPP4, DYM, EED, EFCAB4B, EPC1, ERAP1, FAM122C, FAM13B, FAM178A, FAS, FBXO21, GALNS, GBP2, GSTM1, HLA-A, HYDIN, IFI16, IL6ST, KIAA0174, KIAA1009, KIAA1328, KLHL2, KRT14, LEPR, LNPEP, LOC652614, LRRK1, MAN2A1, MAP3K1, MBD1, MT1X, MTSS1, MTUS1, NAPG, NRBP2, OGN, PCNX, PDK4, PHACTR2, PHLPP, PI15, PITPNC1, PLAA, PLEKHF2, PRKD3, PSEN1, PSMB8, PSPC1, RAB11FIP2, RBBP7, RBBP8, RBM41, RGS2, RGS22, RND3, RNPC3, RPRD1A, SATB1, SCN7A, SDCCAG10, SETBP1, SH3RF2, SLC15A2, SPG7, SQRDL, SRD5A2, ST6GAL1, SYNCRIP, TNFRSF10D, TNRC6A, TRIM22, ZADH2, ZBTB20, ZNF259, ZNF334, and ZNF532 are indicative of a poor prognosis. Thus, alteration in the expression of 5, 6, 7, 8, 9, 10, 15, 20, 25, 30, 40, 50, 60, 70 or all of these genes, in the manner described, is indicative of a poor prognosis. Any number of these genes may be analyzed as long as the specified number of genes has the specified expression modulation. An indication of poor prognosis would warrant aggressive therapy on such a patient.

In one embodiment of the present invention, the analyzing step is performed following surgical removal of the prostate tumor or following another definitive treatment. In that case, the prognosis is for recurrence of the disease. A good prognosis means likelihood that there will be no recurrence. A poor prognosis means a likelihood of recurrence.

In another embodiment of the present invention, the analyzing step is performed prior to surgical removal of the prostate tumor or other definitive treatment. In that case, the prognosis is for the necessity of surgical removal or other definitive treatment. A good prognosis, indicating the likelihood that the tumor will be very slow growing and likely to remain in quiescence for years, may militate against immediate surgery or other definitive treatment. These patients would fall into the "watchful waiting" or "active surveillance" category. On the other hand, a poor prognosis would suggest the necessity of immediate surgery or other definitive treatment.

The present invention is also directed to kits that may be used for practicing any of the methods of the present invention. Such kits will include a set of affinity reagents that will specifically detect expression of the specific genes, the expression levels of which are used in the analysis of the methods of the present invention. For example, in one example of such a kit, affinity reagents would be included that will specifically detect any of at least 2, 3, 4, 5, 6, 7, 8 9, 10, 11 or 12 genes or gene products within the group JUNB, KLF4, FOXH1, FOS, CLDN4, PADI4, B3GNT5, CDC7, PANK1, UNG, CBR3, and ATF3. Alternatively, the kit could include affinity reagents that will specifically detect any of at least 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, or 185 genes or gene products within the group ACAT1, ANLN, ARHGDIG, ASPN, BNC1, BRCA1, BUB1B, C13ORF3, C6ORF105, C8ORF34, CASC5, CCNA2, CDKN3, CENPF, CENPI, CHPF, CIT, DEGS1, DIRAS2, DLGAP5, DNAH8, DUSP26, E2F8, EFNA3, ELFN2, EME1, EPHA6, ESPL1, EVPL, FAP, FKBP10, FOLH1, HBE1, HCG_1774568, IGF2BP3, INCENP, IRS4, IVL, KIF11, KIF4A, KIF4B, KRT1, LOC654342, MELK, MKI67, MLF1IP, NCAPG, NCAPG2, NFS1, NOX4, NUSAP1, ONECUT2, PRC1, PRR3, PSAPL1, PSAT1, PTPRR, RACGAP1, RAMP2, RELN, RP11-49G10.8, SCGN, SLC2A13, SLC31A2, SLC35F1, SLC6A10P, SMC2, SYT9, TAS2R10, TEX101, THSD1, TPX2, TSSC1, TTK, UBE2C, UNC13C, USP9Y, UTS2D, WNT4, WT1, ZFP41, AASDHPPT, ACIN1, ACSL5, ACTN1, AHNAK, ANKRA2, ANKRD36, ANO5, ANXA1, ASCC3, B4GALT1, BACE2, BTBD3, C10ORF26, C18ORF25, CASP4, CD44, CDK10, CEP110, CHD3, COG4, CTR9, CWF19L2, CYP1B1, CYP27A1, DDHD2, DDX6, DENND2D, DPP4, DYM, EED, EFCAB4B, EPC1, ERAP1, FAM122C, FAM13B, FAM178A, FAS, FBXO21, GALNS, GBP2, GSTM1, HLA-A, HYDIN, IFI116, IL6ST, KIAA0174, KIAA1009, KIAA1328, KLHL2, KRT14, LEPR, LNPEP, LOC652614, LRRK1, MAN2A1, MAP3K1, MBD1, MT1X, MTSS1, MTUS1, NAPG, NRBP2, OGN, PCNX, PDK4, PHACTR2, PHLPP, PI15, PITPNC1, PLAA, PLEKHF2, PRKD3, PSEN1, PSMB8, PSPC1, RAB11FIP2, RBBP7, RBBP8, RBM41, RGS2, RGS22, RND3, RNPC3, RPRD1A, SATB1, SCN7A, SDCCAG10, SETBP1, SH3RF2, SLC15A2, SPG7, SQRDL, SRD5A2, ST6GAL1, SYNCRIP, TNFRSF10D, TNRC6A, TRIM22, ZADH2, ZBTB20, ZNF259, ZNF334, and ZNF532.

The affinity reagents are preferably arranged on a microarray. Preferably, the microarray used is one created for use with the methods of the present invention and include only affinity reagents for detecting gene or protein expression of the genes discussed herein, along with a number of control genes, such as housekeeping genes, for use in normalization of the results. Preferably, the microarray would contain no more than about 25, 20, 15, or 10 affinity reagents for control genes or protein products expressed thereby. A microarray for use in the kit of the present invention preferably includes fewer than 2,501 affinity reagents, more preferably fewer than 626, most preferably fewer than 101. Preferably, such a microarray includes affinity reagents specific for no more than 10,000, 5,000, 4,000 or 3,000 total affinity reagents.

The kit of the present invention may comprise a signal producing system whereby the detection of the marker of expression (encoding mRNA, corresponding cDNA, expressed polypeptide, or downstream product of expression) is revealed. The signal producing system may comprise a radioactive, enzymatic or fluorescent label (e.g., Cy3 or Cy5), which may be attached directly or indirectly to the affinity reagent. If the labeling is indirect, the kit may comprise a labeled secondary reagent (such as a nucleic acid, peptide, or antibody or antigen-specific antibody fragment) that binds to the affinity reagent. For example, if the affinity reagent is a nucleic acid, all of the affinity reagents may comprise the same tag (nucleic acid or otherwise), and the secondary reagent binds to the tag. If the label is enzymatic, the kit may comprise a substrate for the enzyme that is converted into a colored product by the action of that enzyme.

BRIEF DESCRIPTION OF THE DRAWINGS

The patent or application file contains at least one drawing executed in color. Copies of this patent or patent application publication with color drawings will be provided by the Office upon request and payment of the necessary fee.

FIG. 18A shows the histology of the small tumor formed by the AKT cell line. It can be seen that this cell line formed small PIN lesions. FIG. 18B shows the histology of the tumor formed by the AKT/KLF4 KD cell line. It can be seen that this cell line formed highly invasive sarcomatoid carcinomas under the renal capsule (RC). Solid arrows show invasion into kidney tissue. Open arrowheads show normal kidney tissue. The scale bar is equal to 30 µm.

DEFINITIONS

Figure 1:
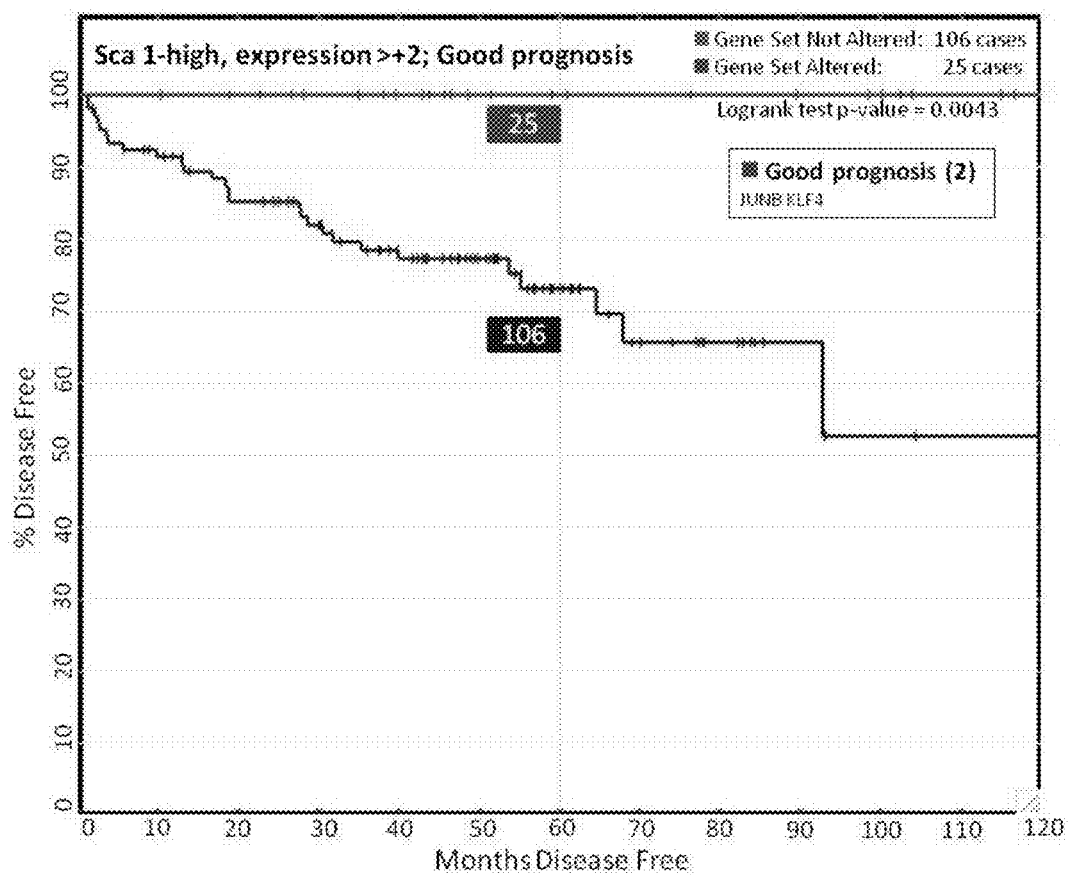
FIG. 1 is a Kaplan-Meier plot of 131 prostate cancer patients in the MSKCC database separated into two outcome groups based on up-regulation of genes found in the Sca t-high subset (adult stem cells). The separation of the two groups is based on genes whose expression was significantly (p-value ≤0.05) up-regulated by a Z-score of >+2 in five or more patients. In this group, genes were chosen such that their up-regulation in tumors indicated a significantly better disease-free survival than noted for patients whose tumors did not manifest up-regulated expression of these genes.

Unless defined otherwise, technical and scientific terms used herein have the same meaning as commonly understood by one of ordinary skill in the art to which this invention belongs. Singleton et al., Dictionary of Microbiology and Molecular Biology 2nd ed., J. Wiley & Sons (New York, N.Y. 1994), and March, Advanced Organic Chemistry Reactions, Mechanisms and Structure 4th ed., John Wiley & Sons (New York, N.Y. 1992), is one example of a general guide to many of the terms used in the present application.

One skilled in the art will recognize many methods and materials similar or equivalent to those described herein, which could be used in the practice of the present invention. Indeed, the present invention is not to be construed as limited to the methods and materials described herein. For purposes of the invention, the following terms are defined below.

The terms "tumor" and "lesion" as used herein, refer to all neoplastic cell growth and proliferation, whether malignant or benign, and all pre-cancerous and cancerous cells and tissues. Those skilled in the art will realize that a tumor tissue sample may comprise multiple biological elements such as one or more cancer cells, partial or fragmented cells, tumors in various stages, surrounding histologically normal-appearing tissue, and/or macro or micro-dissected tissue.

The terms "cancer" and "cancerous" refer to, or describe, the physiological condition in mammals that is typically characterized by unregulated cell growth and invasion. Examples of cancer in the present invention include, but are not limited to cancer of the urogenital tract, such as prostate cancer, as well as breast, brain and hematopoietic cancers.

The "pathology" of cancer includes all phenomena that affect the well-being of the cancer patient. This includes, without limitation, abnormal or uncontrollable cell growth, metastasis, interference with the normal functioning of neighboring cells, release of cytokines or other secretory products at abnormal levels by normal or tumor cells, suppression or aggravation of inflammatory or immunological response, neoplasia, premalignancy, malignancy, invasion of surrounding or distant tissues or organs, such as lymph nodes, etc.

As used herein, the term "prostate cancer," in the broadest sense, refers to all stages and all forms of cancer arising from the cells and tissue of the prostate gland.

According to the tumor, node, metastasis (TNM) staging system of the American Joint Committee on Cancer (AJCC), AJCC Cancer Staging Manual (7th Ed., 2010), the various stages of prostate cancer are defined as follows: Tumor: T1: clinically inapparent tumor not palpable or visible by imaging; T1a: histological finding of tumor in 5% or less of tissue resected; T1b: histological finding of tumor in more than 5% of tissue resected; T1c: tumor identified by needle biopsy; T2: tumor confined within the prostate; T2a: tumor involves one half of one lobe or less; T2b: tumor involves more than half of one lobe, but not both lobes; T2c: tumor involves both lobes; T3: tumor extends through the prostatic capsule; T3a: extracapsular extension (unilateral or bilateral); T3b: tumor invades seminal vesicle(s); T4: tumor is fixed or invades adjacent structures other than seminal vesicles (bladder neck, external sphincter, rectum, levator muscles, or pelvic wall). Node: N0: no regional lymph node metastasis; N1: metastasis in regional lymph nodes. Metastasis: M0: no distant metastasis; M1: distant metastasis present.

The Gleason grading system is used to help evaluate the prognosis of men with prostate cancer. Together with other parameters, it is incorporated into a strategy of prostate cancer staging, which predicts prognosis and helps guide therapy. The Gleason grading system is based on the glandular pattern of the tumor. Gleason grade takes into account the ability of the tumor to form glands. A pathologist, using relatively low magnification, performs the histologic review necessary for assigning the Gleason grade. The range of grades is 1-5: 1, 2 and 3 are considered to be low to moderate in grade; 4 and 5 are considered to be high grade. The prognosis for a given patient generally falls somewhere between that predicted by the primary grade given to the most prominent pattern and a secondary grade given to the second most prominent pattern. When the two grades are added, the resulting number is referred to as the Gleason score. The Gleason score is a more accurate predictor of outcome than either of the individual grades. Thus, the traditionally reported Gleason score will be the sum of two numbers between 1-5 that yield a total score of 2-10. It is unusual for the primary and secondary Gleason grade to differ by more than one, such that the only way that there can be a Gleason score 7 tumor is if the primary or secondary Gleason grade is 4. Because of the presence of grade 4 patterns in tissue having Gleason score 7, these tumors can behave in a much more aggressive fashion than those having Gleason score 6. In a recent study of over 300 patients, the average disease specific survival for Gleason score 7 patients was 10 years. In contrast, the average survival of Gleason score 6 patients was 16 years and the average survival for Gleason 4-5 was 20 years. It is therefore clear that the prognosis for men with Gleason score 7 tumors is worse than for men with Gleason score 5 and 6 tumors. There are indications that patients with Gleason score 7 tumors might have different prognosis depending on whether the tumor is Gleason 3+4 (92.1% 10 year survival) vs. Gleason 4+3 (76.5% 10 year survival). (Wright J L et al, "Prostate cancer specific mortality and Gleason 7 disease differences in prostate cancer outcomes between cases with Gleason 4+3 and Gleason 3+4 tumors in a population based cohort" *J Urol.* 182(6):2702-7 (2009)). Thus, under certain circumstances it is suggested that men with Gleason 7 tumors can be considered for more aggressive therapy.

Tumors with a low Gleason score typically grow slowly enough that they may not pose a significant threat to the patients in their lifetimes. These patients are monitored ("watchful waiting" or "active surveillance") over time. Cancers with a higher Gleason score are more aggressive and have a worse prognosis, and these patients are generally treated with surgery (e.g., radical prostatectomy) and, in some cases, adjuvant therapy (e.g., radiation, hormone, ultrasound and/or chemotherapy). The ability to stratify individuals having a Gleason score of 6 and 7 based on probability of relapse is significant because these are patients in which critical decisions must be made regarding therapies beyond surgery. Stage groupings: Stage I: T1a N0 M0 G1; Stage II: (T1a N0 M0 G2-4) or (T1b, c, T1, T2, N0 M0 Any G); Stage III: T3 N0 M0 Any G; Stage IV: (T4 N0 M0 Any G) or (Any T N1 M0 Any G) or (Any T Any N M1 Any G).

As used herein, the term "tumor tissue" refers to a biological sample containing one or more cancer cells, or a fraction of one or more cancer cells. Those skilled in the art will recognize that such a biological sample may additionally comprise other biological components, such as histologically normal-appearing cells (e.g., adjacent to the tumor), depending upon the method used to obtain the tumor tissue, such as surgical resection, biopsy, or bodily fluids.

As used herein, the term "AUA risk group" refers to the 2007 updated American Urological Association (AUA) guidelines for management of clinically localized prostate cancer, which clinicians use to determine whether a patient is at low, intermediate, or high risk of biochemical (PSA) relapse after local therapy.

Prognostic factors are those variables related to the natural history of cancer, which influence the recurrence rates and outcome of patients once they have developed cancer. Clinical parameters that have been associated with a worse prognosis include, for example, increased tumor stage, PSA level at presentation, and Gleason grade or pattern. Prognostic factors are frequently used to categorize patients into subgroups with different baseline relapse risks.

The term "prognosis" is used herein to refer to the likelihood that a cancer patient will have a cancer-attributable death or disease progression, including recurrence, metastatic spread, and drug resistance, of a neoplastic disease, such as prostate cancer. For example, a "good prognosis" would include the likelihood of long term survival without recurrence and a "poor" prognosis would include the likelihood of cancer recurrence.

The terms "good prognosis" or "positive prognosis" as used herein with respect to prostate cancer refer to the likelihood of a beneficial clinical outcome, such as long-term survival without recurrence or progression. The terms "poor prognosis" or "bad prognosis" or "negative prognosis" as used herein with respect to prostate cancer refer to the likelihood of a negative clinical outcome, such as cancer recurrence or disease progression.

The term "recurrence" is used herein to refer to local or distant recurrence (i.e., metastasis) of cancer. For example, prostate cancer can recur locally in the tissue near the prostate or in the seminal vesicles. This cancer may also affect the surrounding lymph nodes in the pelvis or lymph nodes outside this area. Prostate cancer can also spread to more distant tissues, such as pelvic muscles and organs, bones, or organs beyond the pelvis. Recurrence can be determined as clinical recurrence detected by, for example, imaging studies or biopsy, or as biochemical recurrence detected by, for example, increasing PSA levels or the initiation of salvage therapy as a result of an increasing PSA level.

As used herein, the term "expression level" as applied to a gene refers to the normalized level of a gene product, e.g., the normalized value determined for the RNA transcribed from a gene or for the expression level of the polypeptide encoded by a gene. The terms "gene product" or "expression product" are used herein to refer to the RNA (ribonucleic acid) transcription products (transcripts) of the gene, including mRNA, and the polypeptide translation products of such RNA transcripts. A gene product can be, for example, an unspliced RNA, an mRNA, a splice variant mRNA, a microRNA, a fragmented RNA, a polypeptide, which may be a post-translationally modified polypeptide, a splice variant polypeptide, etc.

The term "Z-score," for mRNA and microRNA expression data, represents the relative expression of an individual gene in a tumor to the gene's expression distribution in a reference population. The reference population is either all tumors that are diploid for the gene in question, or, when available, normal adjacent tissue. The returned value indicates the number of standard deviations away from the mean of expression in the reference population (Z-score). This measure is useful to determine whether a gene is up- or down-regulated relative to the normal samples or all other tumor samples.

The term "RNA transcript" as used herein refers to the RNA transcription product of a gene, including, for example, mRNA, unspliced RNA, a splice variant mRNA, a microRNA, and a fragmented RNA.

The term "microRNA" ("miRNA") is used herein to refer to a small, non-coding, single-stranded RNA of approximately 18-25 nucleotides that may regulate gene expression. For example, when the miRNA is associated with the RNA-induced silencing complex (RISC), the complex binds to a specific mRNA target and causes translation repression or cleavage of the mRNA.

Unless indicated otherwise, each gene name used herein corresponds to the Official Symbol assigned to the gene and provided by Entrez Gene (URL: www.ncbi.nlm.nih.gov/sites/entrez) as of the filing date of this application.

The terms "correlated" and "associated" are used interchangeably herein to refer to the association between two measurements (or measured entities). The disclosure provides genes, gene subsets, mRNAs, or microRNAs in combination with genes or gene subsets, the expression levels of which are associated with tumor stage. For example, the increased expression level (up-regulated, up-modulated) of a gene or microRNA may be positively associated or correlated with a good or positive prognosis. Such a positive correlation may be demonstrated statistically in various ways, e.g., by a cancer recurrence hazard ratio of less than one. In another example, the increased expression level of a gene or microRNA may be negatively associated or correlated with a good or positive prognosis. In that case, for example, the patient may experience a cancer recurrence.

When used with respect to a gene found in stem cells, either adult or fetal, the term "uniquely up-regulated" means that the expression of that gene is up-regulated as compared to the level of expression of that gene in fully differentiated cells of the tissue.

When used with respect to a gene found in a tumor cell originating from a particular tissue, the terms "up-regulated," "down-regulated" or "modulated" mean that the expression of that gene is up-regulated, down-regulated or modulated as compared to the level of expression of that gene in non-tumor cells of the same tissue or the tumor cells of that tissue from a plurality of other patients.

The term "risk classification" means a grouping of subjects according to the level of risk (or likelihood) that the subject will experience a particular clinical outcome. A subject may be classified into a risk group or classified at a level of risk based on the methods disclosed herein, e.g., high, medium, or low risk. A "risk group" is a group of subjects or individuals (e.g., patients) with a similar level of risk for a particular clinical outcome. Those designated, by means of the present invention, as having a good prognosis would be classified in the low risk classification, while those designated, by means of the present invention, as having a poor prognosis would be classified in the high risk classification.

The term "long-term" survival is used herein to refer to survival for a particular time period, e.g., for at least 5 years, or for at least 10 years.

As used herein, the terms "active surveillance" and "watchful waiting" mean closely monitoring a patient's condition without giving any treatment until symptoms appear or change. For example, in prostate cancer, watchful waiting is usually used in older men with other medical problems and early-stage disease.

As used herein, the term "surgery" applies to surgical methods undertaken for removal of cancerous tissue, including pelvic lymphadenectomy, radical prostatectomy, transurethral resection of the prostate (TURP), excision, dissection, and tumor removal. The tumor tissue or sections used for gene expression analysis may have been obtained from any of these methods. They also may have been obtained by non-surgical methods, such as biopsy.

As used herein, the term "therapy" includes radiation, hormonal therapy, cryosurgery, chemotherapy, biologic therapy, and high-intensity focused ultrasound.

DETAILED DESCRIPTION OF THE INVENTION

The present invention originated with the idea that genes of the adult prostate stem cells (APSC) that are uniquely up-regulated in APSCs, in comparison to the expression of genes in fully differentiated cells of the same tissue, would contribute to quiescence of prostate tumor cells if their expression is up-regulated in those cells. Thus, up-regulation of the expression of such genes in human prostate cancer cells would indicate a good prognosis. Therefore, the present inventors' laboratory performed microarray analysis of candidate stem and progenitor cell populations in the mouse to identify molecular signatures and signaling pathways in prostate stem cells (Blum R, et al., "Molecular signatures of prostate stem cells reveal novel signaling pathways and provide insights into prostate cancer," *PLoS One* 4(5):e5722 (2009); Blum R, et al., "Molecular signatures of the primitive prostate stem cell niche reveal novel mesenchymal-epithelial signaling pathways," *PLoS One*; 5(9):e13024 (2010), the entire contents of both of which being hereby incorporated herein by reference). The transcriptional profiles of four populations of cells were determined:

(i) urogenital sinus epithelium (UGE), enriched in fetal prostate stem cells (FPSC), (ii) Sca 1-high cells that express high levels of Sca 1, enriched in adult prostate stem cells (APSC) (Burger P E, et al., "Sca-1 expression identifies stem cells in the proximal region of prostatic ducts with high capacity to reconstitute prostatic tissue," *Proc Natl Acad Sci USA* 102(20):7180-85 (2005); Xin L, et al., "The Sca-1 cell surface marker enriches for a prostate-regenerating cell subpopulation that can initiate prostate tumorigenesis," *Proc Natl Acad Sci USA* 102(19): 6942-47 (2005), the entire contents of both of which being hereby incorporated herein by reference), (iii) Sca 1-medium/low cells that express medium to low levels of Sca 1 and are enriched in transit-amplifying cells with limited growth potential (Burger 2005, supra) and (iv) Sca 1-negative cells with no Sca 1 expression, that represent the most mature population and have almost no regenerative potential (Burger 2005, supra).

It was determined that APSCs and FPSCs had many uniquely up-regulated genes, as compared to the level of expression of those genes in fully differentiated prostate cells. Among the APSC-specific genes were peptidylarginine deiminase type IV (PADI4), over-expressed 27-fold, and two transcription factors KLF4 and JUNB. Active TGF-β, generated by APSCs, was under the control of PADI4; its knockdown reduced active TGF-β and enhanced cell proliferation in 3D culture and in vivo, indicating that PADI4 is a quiescence-inducing gene. This is the first demonstration that PADI4 is over-expressed and has an important function in stem cells. Microarray analysis indicated that many genes whose expression is altered in fetal stem cells are involved in proliferation and self-renewal, while a number of genes with altered expression in adult stem cells show a gene expression signature in which quiescence predominates (Blum 2009, supra). Adult stem cells express high levels of a number of molecules that restrict growth of primitive cells such as TGF-β (Salm S N, et al., "TGF-β maintains dormancy of prostatic stem cells in the proximal region of ducts," *Journal of Cell Biology* 170(1):81-90 (2005)), aldehyde dehydrogenase (Muramoto G G, et al., "Inhibition of aldehyde dehydrogenase expands hematopoietic stem cells with radioprotective capacity," *Stem Cells* 28(3):523-534 (2010); Burger P E, et al., "High aldehyde dehydrogenase activity: a novel functional marker of murine prostate stem/progenitor cells," Stem cells (Dayton, Ohio) 27(9):2220-2228 (2009)), the aryl hydrocarbon receptor (Boitano A E, et al., "Aryl hydrocarbon receptor antagonists promote the expansion of human hematopoietic stem cells," *Science* 329:1345-48 (2010)) and peptidylarginine deiminase type IV (PADI4). They also express high levels of JUNB, KLF4, FOXH1 and CLDN4 (see FIG. 2B from Blum 2009, supra)).

To confirm whether genes expressed in adult prostate stem cells could predict the length of disease-free survival in patients with prostate cancer, the database emanating from the genomic profiling of human prostate cancer (Taylor B S, et al., "Integrative genomic profiling of human prostate cancer," *Cancer Cell* 18(1):11-22 (2010)) that can be accessed and explored through the MSKCC Prostate Cancer Genomics Data Portal at www.cbioportal.org/public-portal/index.do?cancer_study_id=mskcc_prad was interrogated. This database contains mRNA profiles, the follow-up clinical/pathological information and the disease-free survival data for 131 patients with primary prostate cancer. An investigation of the predictive ability of various genes was carried out. Biochemical relapse was defined as PSA >0.2 ng/ml on two occasions.

Although the adult and fetal stem cell populations that were isolated for gene expression analysis (Blum 2009, supra) were of murine origin, 99% of mouse genes have homologues in man and of these, 96% are in the same syntenic location (genes appear in the same order in the two genomes) in man as in mouse (www.evolutionpages.com/Mouse%20genome%20home.htm). Genes identified in fetal rat liver stem cells can be used to predict the prognosis of human liver cancer patients (Ju-Seog Lee et al, "A novel prognostic subtype of human hepatocellular carcinoma derived from hepatic progenitor cells," *Nature Med* 12, 410-416 (2006)). Thus, it would be expected that the genes identified as being uniquely up-regulated in murine adult and fetal stem cells would be similarly uniquely up-regulated in human cells. Furthermore, their relevance to the present invention was proven by the analysis of the human prostate tumor gene modulation data from the MSKCC database, discussed herein. KLF4 and JUNB were over-expressed in 27/131 patients and these patients had a remarkable 100% relapse-free survival for up to 10 years. PADI4 up-regulation was too infrequent for statistical evaluation. A highly significant prediction (p=0.000668) of 100% disease-free survival in 25.2% of patients with primary prostate cancer was obtained for patients whose tumors expressed a combination of KLF4, JUNB and FOS. FOS was added as members of the FOS family dimerize with members of the JUN family to form the AP-1 transcription factor. If FOXH1 was added to this combination of three genes, the p value improved slightly (p=0.000461). It is important to note that none of the patients whose tumors expressed these combinations of genes had a biochemical relapse during their follow-up of up to 10 years.

To investigate further the relationship of APSC genes to long-term survival in the MSKCC database, an analysis was conducted to encompass all the genes whose expression was found to be modulated in the Sca 1-high subset, numbering 302 genes (represented by 641 probes) (see FIG. 1 from Blum 2009, supra). Table 3 shows the gene, the fraction of disease-free patients and the p-value for the logrank test: only those genes for which the separation of the two groups based on a gene expression Z-score of >+2 in five or more patients was significant, as judged by a p-value less than or equal to 0.05, were considered. Two genes, JUNB and KLF4, predicted at least 10-year biochemical relapse-free survival in roughly 20% of patients. The Kaplan-Meier plot of disease-free survival of patients whose tumor cells expressed these two genes is shown in FIG. 1. This confirms the predictions made, above. While no other genes were found that are uniquely up-regulated in Sca 1-high cells whose up-regulation in tumors was predictive of good outcome, i.e., indicative of good prognosis, at the settings indicated above, it is still predicted that PADI4, FOXH1 and CLDN4 would also be indicative of good prognosis if tested against a larger sample of patients.

Figure 6:
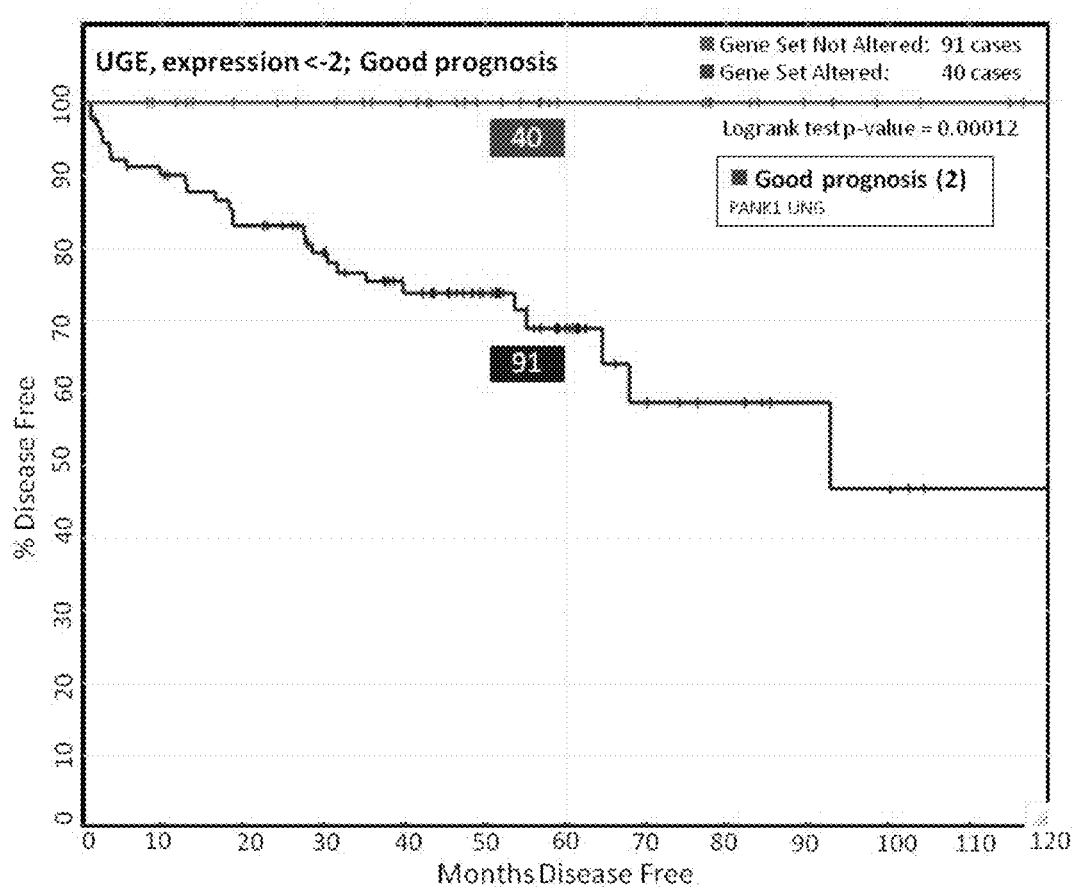
FIG. 6 is a Kaplan-Meier plot of 131 prostate cancer patients in the MSKCC database separated into two outcome groups based on down-regulation of genes found in the UGE subset (fetal stem cells). The separation of the two groups is based on genes whose expression was significantly (p-value ≤0.05) down-regulated by a Z-score of <−2 in five or more patients. In this group, genes were chosen such that their down-regulation in tumors indicated a significantly better disease-free survival than noted in patients whose tumors did not manifest down-regulated expression of these genes.

As genes uniquely up-regulated in the FPSC population, i.e., UGE cells, were predicted to be indicative of poor prognosis, in view of the fact that FPSC cells were highly proliferative, which is often a trait in common with particularly virulent tumors, it was predicted that certain genes uniquely up-regulated in UGE cells, that were down-regulated in the tumors, would be indicative of good prognosis. Accordingly, an analysis was conducted of the MSKCC database to encompass all the genes whose expression was modulated in the UGE subset, numbering 953 genes (represented by 1286 probes) (Blum 2009, supra). Table 6 shows the gene, the fraction of disease-free patients and the p-value for the logrank test: only those genes for which the separation of the two groups based on a gene expression Z-score of <−2, in five or more patients, was significant, with a p-value equal to or less than 0.05, were considered. Down-regulated expression of two genes, PANK1 and UNG, predicted at least 10-year biochemical relapse-free survival in roughly 30% of patients. The Kaplan-Meier plot of disease-free survival of patients whose tumor cells expressed these two genes is shown in FIG. 6. Accordingly, these genes were also added to the group of genes that were indicative of good prognosis on the basis of biological stem cell gene considerations.

Figure 4:
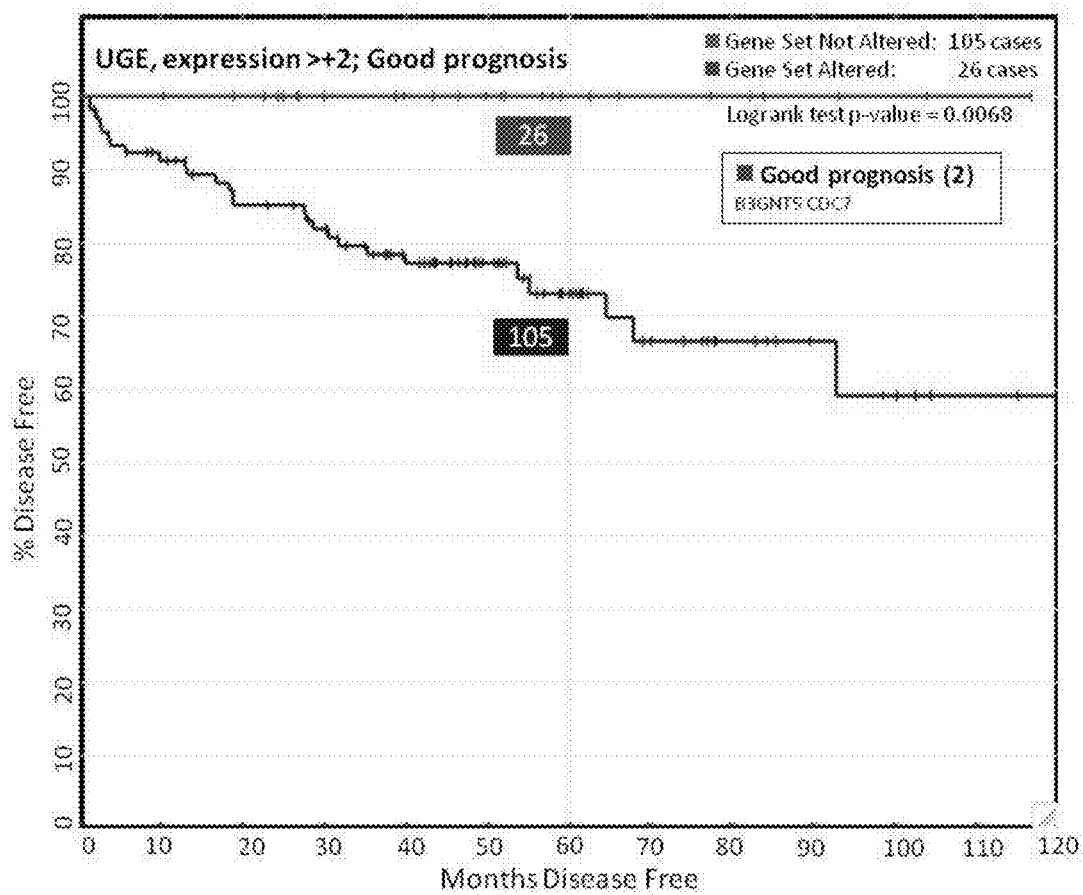
FIG. 4 is a Kaplan-Meier plot of 131 prostate cancer patients in the MSKCC database separated into two outcome groups based on genes found to be uniquely up-regulated in the UGE subset (fetal stem cells). The separation of the two groups is based on genes whose expression was significantly (p-value ≤0.05) up-regulated by a Z-score of >+2 in five or more patients. In this group, genes were chosen such that their up-regulation in tumors indicated a significantly better disease-free survival than noted for patients whose tumors did not manifest up-regulated expression of these genes.

In the course of the analyses involving genes uniquely up-regulated in the UGE (fetal stem cells), it was unexpectedly found that the up-regulation of two such genes was indicative of good prognosis. An analysis was conducted to encompass all the genes in the UGE subset, numbering 953 genes (represented by 1286 probes). Table 5 shows the gene, the fraction of disease-free patients and the p-value for the logrank test: only those genes for which the separation of the two groups based on a gene expression Z-score of >+2 in five or more patients was significant, as judged by a p-value less than or equal to 0.05, were considered. Two genes, B3GNT5 and CDC7, predicted at least 10-year biochemical relapse-free survival in roughly 20% of patients. The Kaplan-Meier plot of the disease-free survival of patients whose tumor cells expressed these two genes is shown in FIG. 4. Accordingly, these genes were also added to the group of genes that were indicative of good prognosis on the basis of biological stem cell gene considerations.

None of the genes uniquely up-regulated in the adult stem cells (Sca 1-high cells) that were down-regulated in tumor cells were found to be indicative of good prognosis.

Figure 5:
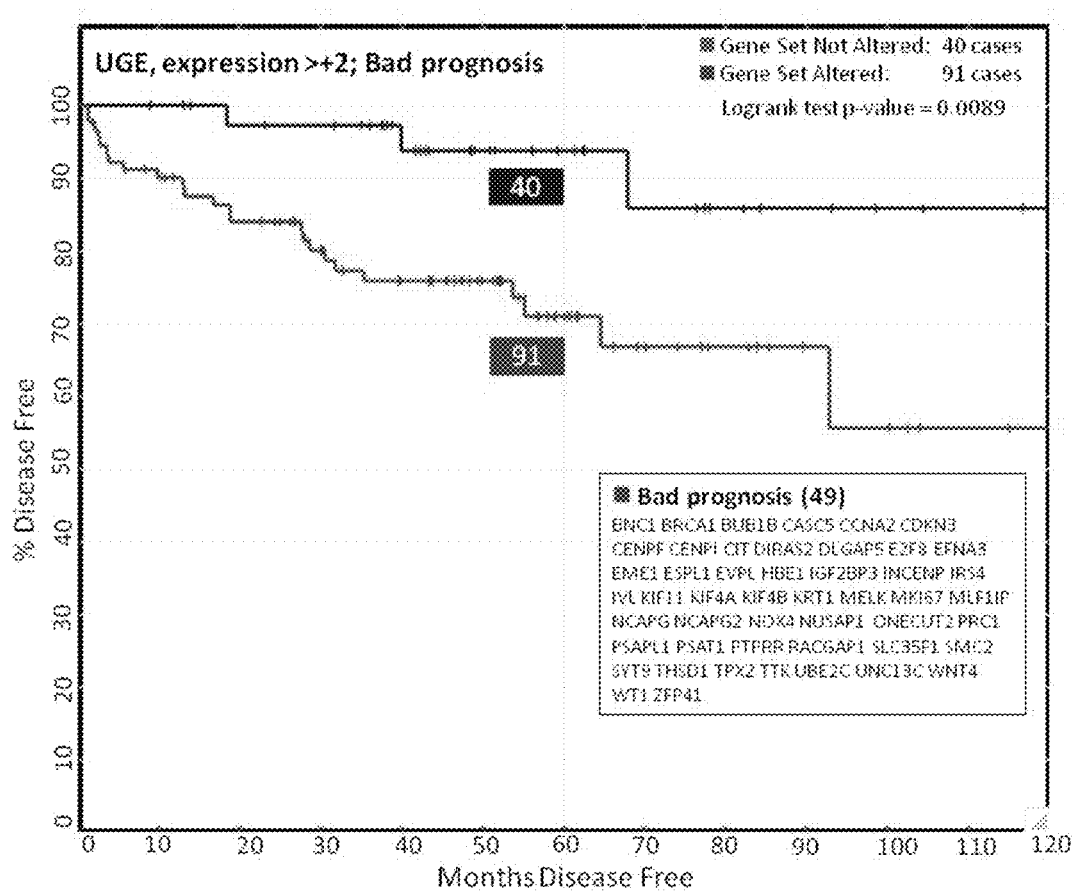
FIG. 5 is a Kaplan-Meier plot of 131 prostate cancer patients in the MSKCC database separated into two outcome groups based on up-regulation of genes found in the UGE subset (fetal stem cells). The separation of the two groups is based on genes whose expression was significantly (p-value ≤0.05) up-regulated by a Z-score of >+2 in five or more patients. In this group, genes were chosen such that their up-regulation in tumors indicated a significantly worse disease-free survival than noted in patients whose tumors did not manifest up-regulated expression of these genes.

As genes uniquely up-regulated in FPSCs would be considered to be predictors of bad outcome, i.e., as fetal stem cells have high proliferation, an analysis was conducted to encompass all the genes in the UGE subset, numbering 953 genes (represented by 1286 probes). Table 5 shows the gene, the fraction of disease-free patients and the p-value for the logrank test: only those genes for which the separation of the two groups based on a gene expression Z-score of >+2 in five or more patients was significant, as judged by a p-value less than or equal to 0.05, were considered. Forty nine genes predicted a poor prognosis in 30% of patients. These were: BNC1, BRCA1, BUB1B, CASC5, CCNA2, CDKN3, CENPF, CENPI, CIT, DIRAS2, DLGAP5, E2F8, EFNA3, EME1, ESPL1, EVPL, HBE1, IGF2BP3, INCENP, IRS4, IVL, KIF11, KIF4A, KIF4B, KRT1, MELK, MKI67, MLF1IP, NCAPG, NCAPG2, NOX4, NUSAP1, ONECUT2, PRC1, PSAPL1, PSAT1, PTPRR, RACGAP1, SLC35F1, SMC2, SYT9, THSD1, TPX2, TTK, UBE2C, UNC13C, WNT4, WT1, and ZFP41. The Kaplan-Meier plot of the disease-free survival of patients in whose tumor cells these forty nine genes were up-regulated is shown in FIG. 5. Accordingly, these genes were considered to be a group of genes that were predictors of bad outcome, i.e., indicative of poor prognosis, on the basis of biological stem cell gene considerations.

Figure 3:
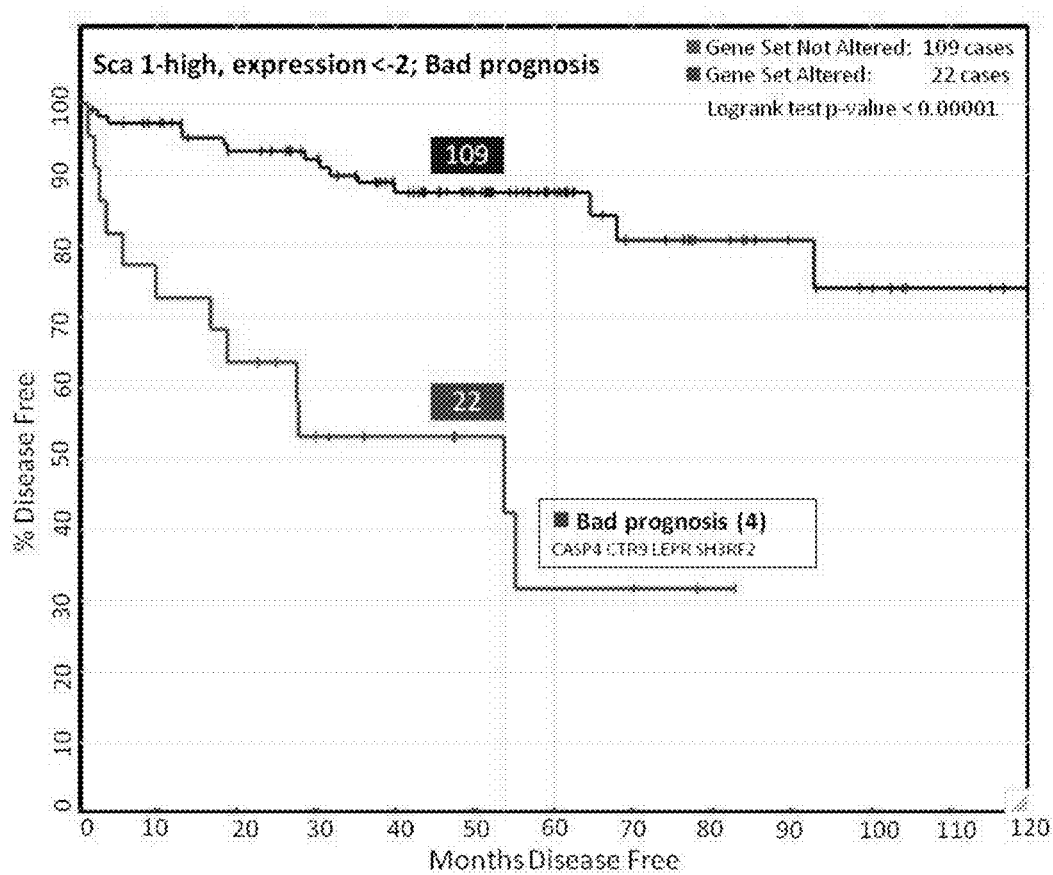
FIG. 3 is a Kaplan-Meier plot of 131 prostate cancer patients in the MSKCC database separated into two outcome groups based on down-regulation of genes found in the Sca 1-high subset (adult stem cells). The separation of the two groups is based on genes whose expression was significantly (p-value ≤0.05) down-regulated to a Z-score of <−2 in five or more patients. In this group, genes were chosen such that their down-regulation in tumors indicated a significantly worse disease-free survival than noted in patients whose tumors did not manifest down-regulation of these genes.

As genes uniquely up-regulated in the APSC population, i.e., Sca 1-high cells, were predicted to be indicative of good prognosis, in view of the fact that APSC cells are phenotypically quiescent, which, if found in tumors, would establish the likelihood of a slowly progressing disease, it was predicted that any genes expressed in Sca 1-high cells (adult stem cells) whose expression was down-regulated in the tumors would be indicative of poor prognosis. Accordingly, an analysis was conducted to encompass all the genes in the Sca 1-high subset, numbering 302 genes (represented by 641 probes). Table 4 shows the gene, the fraction of disease-free patients and the p-value for the logrank test: only those genes for which the separation of the two groups based on a gene expression Z-score of <−2 in five or more patients was significant, as judged by a p-value less than or equal to 0.05, were considered. Down-regulation of the expression of four genes predicted a median survival of 54 months to biochemical relapse in 20% of patients at risk. These were CASP4, CTR9, LEPR, and SH3RF2. The Kaplan-Meier plot of the disease-free survival of patients in whose tumor cells the expression of these four genes was down-regulated is shown in FIG. 3. Accordingly, these genes were added to the group of genes that are considered to be indicative of poor prognosis.

Figure 2:
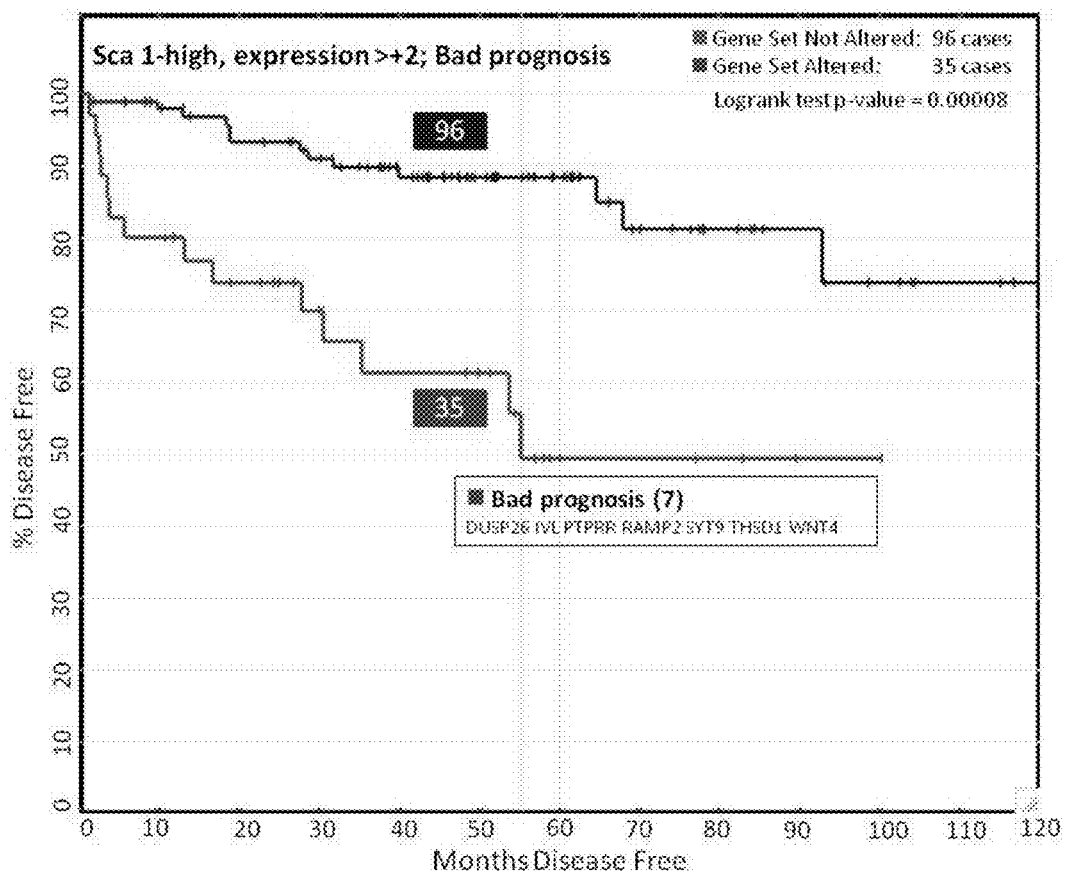
FIG. 2 is a Kaplan-Meier plot of 131 prostate cancer patients in the MSKCC database separated into two outcome groups based on up-regulation of genes expressed in the Sca 1-high subset (adult stem cells). The separation of the two groups is based on genes whose expression was significantly (p-value ≤0.05 expression) up-regulated by a Z-score of >+2 in five or more patients. In this group, genes were chosen such that their up-regulation in tumors indicated a significantly worse disease-free survival than noted for patients whose tumors did not manifest up-regulation of these genes.

In the course of the analyses involving genes expressed in Sca 1-high cells, it was unexpectedly found that the up-regulation of the expression of two such genes was indicative of poor prognosis. An analysis was conducted to encompass all the genes in the Sca 1-high subset numbering 302 genes (represented by 641 probes). Table 3 shows the gene, the fraction of disease-free patients and the p-value for the logrank test: only those genes for which the separation of the two groups based on a gene expression Z-score of >+2 in five or more patients was significant, as judged by a p-value less than or equal to 0.05, were considered. Seven genes predicted a median survival of 56 months to biochemical relapse in 26% of patients. These were DUSP26, IVL, PTPRR, RAMP2, SYT9, THSD1, and WNT4. The Kaplan-Meier plot of the disease-free survival of patients in whose tumor cells the expression of these seven genes was up-regulated is shown in FIG. 2. Accordingly, these genes were added to the group of genes that are considered to be indicative of poor prognosis.

Figure 7:
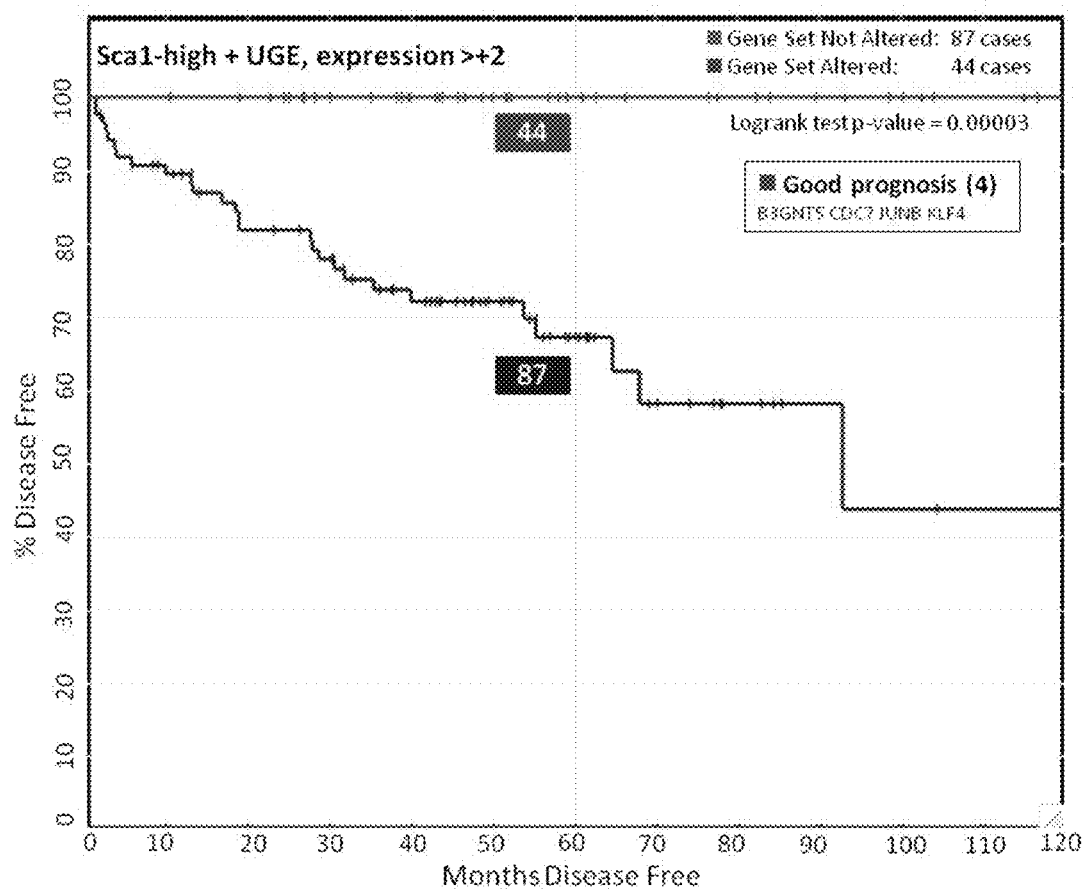
FIG. 7 is a Kaplan-Meier plot of 131 prostate cancer patients in the MSKCC database separated into two outcome groups based on genes found to be up-regulated in both the Sca 1-high (adult stem cells) and UGE (fetal stem cells) subsets. The separation of the two groups is based on genes whose expression was significantly (p-value ≤0.05) up-regulated by a Z-score of >+2 in five or more patients. In this group, genes were chosen such that their up-regulation in tumors indicated a significantly better disease-free survival than noted for patients whose tumors did not manifest up-regulated expression of these genes.

An analysis was conducted to encompass all the genes in the Sca1-high and UGE subset numbering 302 genes (represented by 641 probes) for Sca 1-high plus 953 genes (represented by 1286 probes) for UGE. Only those genes for which the separation of the two groups based on a gene expression Z-score of >+2 in five or more patients was significant as judged by a p-value less than or equal to 0.05 were considered. Four genes, B3GNT5, CDC7, JUNB and KLF4, predicted at least 10-year biochemical relapse-free survival in roughly 34% of patients. These are the same four good prognosis genes discussed above. The Kaplan-Meier plot of the disease-free survival of patients in whose tumor cells the expression of these four genes was up-regulated is shown in FIG. 7.

Figure 8:
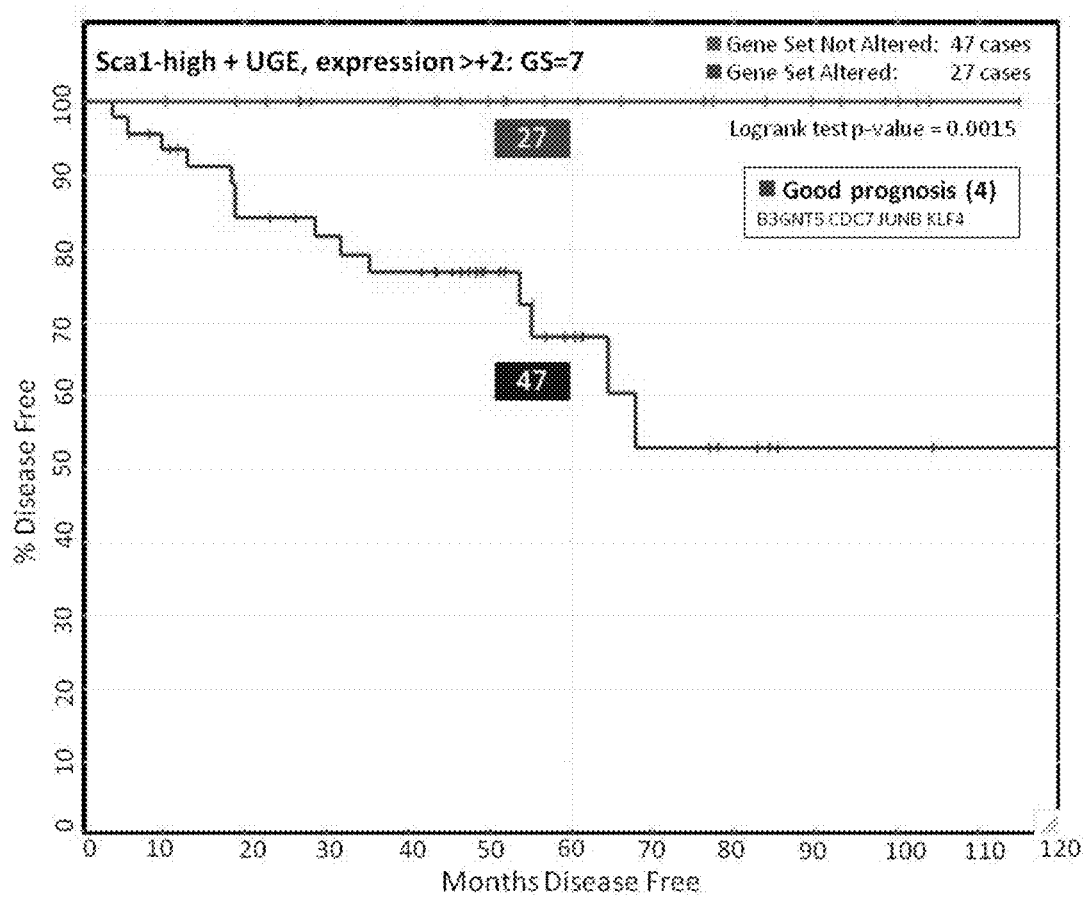
FIG. 8 is a Kaplan-Meier plot of 74 prostate cancer patients in the MSKCC database who were classified as having a Gleason 7 (GS=7) score of cancer and separated into two outcome groups based on genes found to be up-regulated in both the Sca 1-high (adult stem cells) and UGE (fetal stem cells). The separation of the two groups is based on genes whose expression was significantly (p-value ≤0.05) up-regulated by a Z-score of >+2 in five or more patients. In this group, genes were chosen such that their up-regulation in tumors indicated a significantly better disease-free survival than noted for patients whose tumors did not manifest up-regulated expression of these genes.

To make the test even more stringent, an analysis was conducted to encompass all the genes in the Sca1-high (adult stem cells) and UGE subset (fetal stem cells), numbering 302 genes (represented by 641 probes) plus 953 genes (represented by 1286 probes), in patients whose cancer was determined to be Gleason score 7 (GS=7). Only those genes for which the separation of the two groups based on a gene expression Z-score of >+2 in five or more patients was significant, as judged by a p-value less than or equal to 0.05, were considered. The same four genes, B3GNT5, CDC7, JUNB and KLF4, predicted at least 10-year biochemical relapse-free survival in roughly 36% of patients. The Kaplan-Meier plot of the disease-free survival of patients in whose tumor cells expression of these four genes was up-regulated is shown in FIG. 8.

Figure 13:
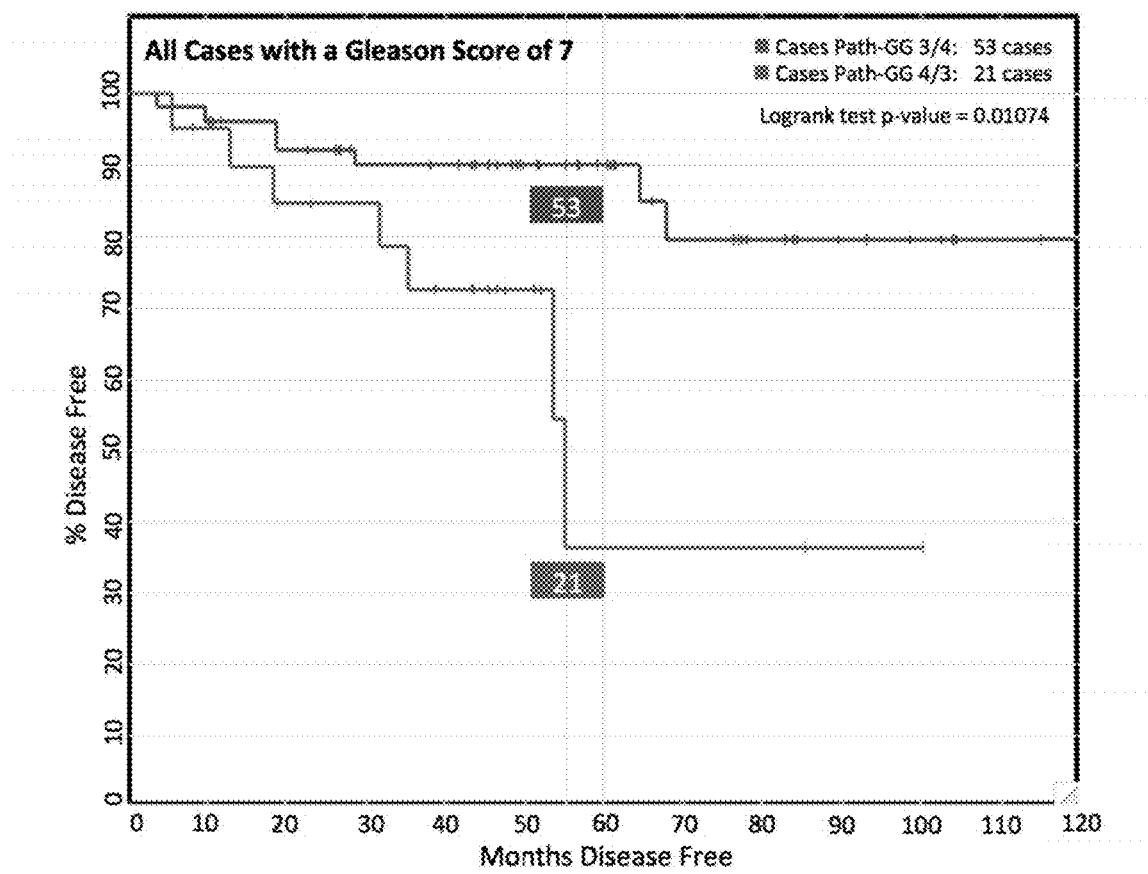
FIG. 13 is a Kaplan-Meier plot of 74 prostate cancer patients in the MSKCC database who were classified as having a Gleason 7 (GS=7) score of cancer separated into two outcome groups based on their primary and secondary Gleason grade determination. The separation of the groups was based on either a primary Gleason grade of 3 and a secondary Gleason grade of 4 (Gleason 3/4) or a primary Gleason grade of 4 and a secondary Gleason grade of 3 (Gleason 4/3). The Gleason 3/4 group (53/74 tumors) had a significantly (p=0.01) better prognosis than the Gleason 4/3 group.
Figure 14:
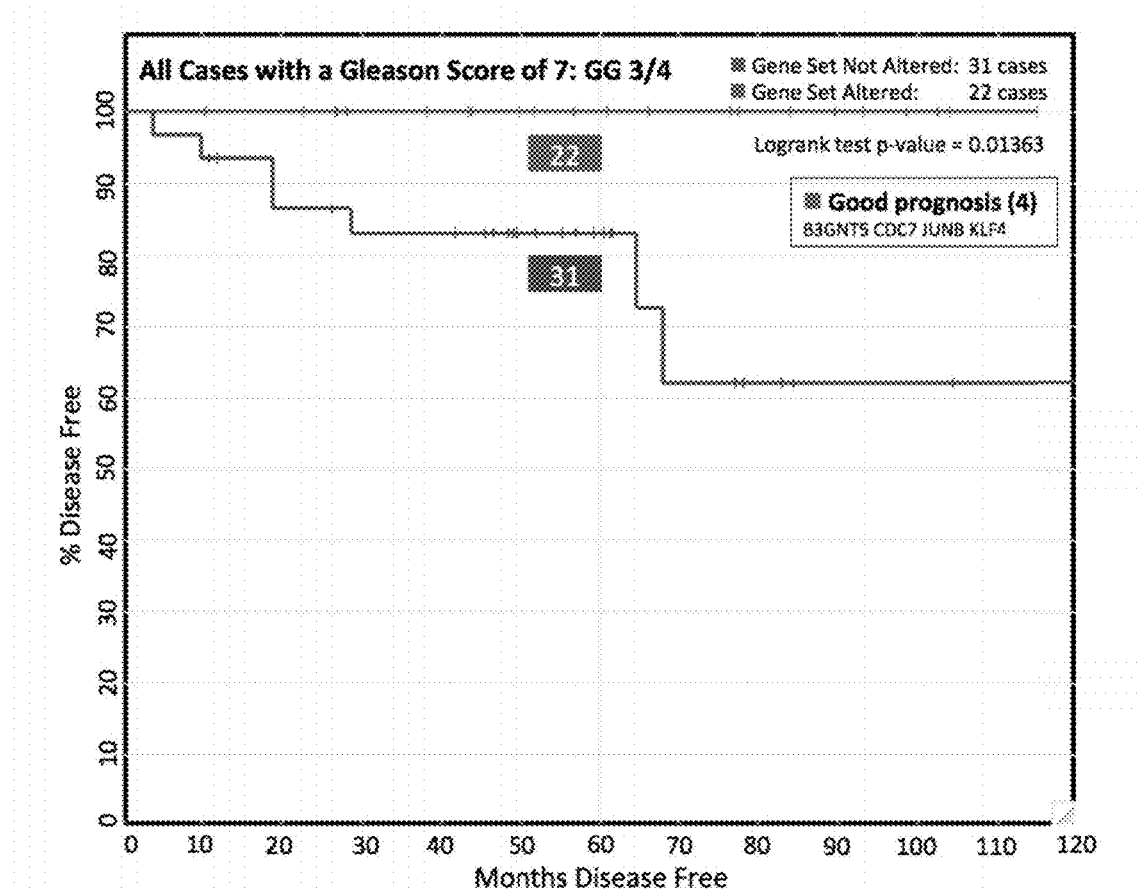
FIG. 14 is a Kaplan-Meier plot of 53 prostate cancer patients in the MSKCC database who were classified as having a Gleason score 7 (Gleason 3/4) separated into two outcome groups based on the up-regulation of good prognosis genes (FIG. 7) found to be over-expressed by a Z-score of >+2 in both the Sca 1-high (adult stem cells) and UGE (fetal stem cells) subsets. These genes further stratified patients with a Gleason score 7 (Gleason 3/4) into 22 patients with no recurrence within 10 years and 31 patients who exhibited a 40% recurrence rate (p=0.013).
Figure 15:
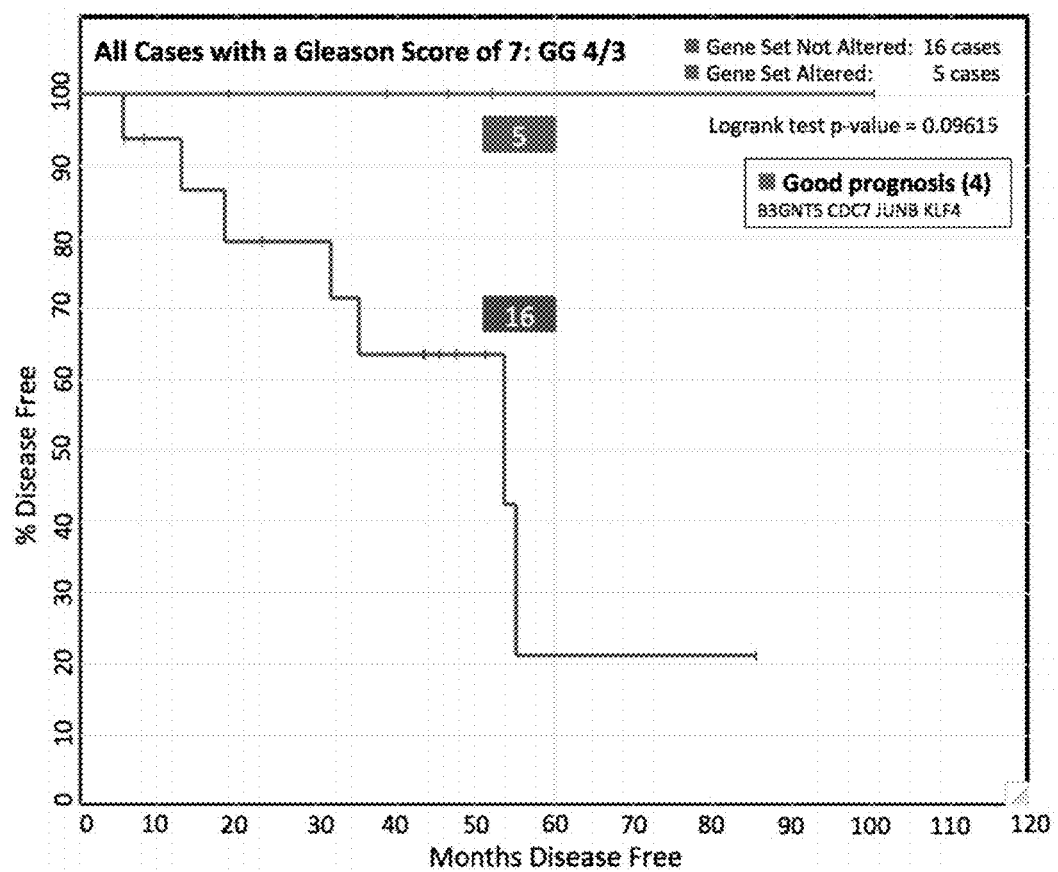
FIG. 15 is a Kaplan-Meier plot of 21 prostate cancer patients in the MSKCC database who were classified as having a Gleason score 7 (Gleason 4/3) separated into two outcome groups based on the up-regulation of good prognosis genes (FIG. 7) found to be over-expressed by a Z-score of >+2 in both the Sca 1-high (adult stem cells) and UGE (fetal stem cells) subsets. These genes further stratified patients with a Gleason score 7 (Gleason 4/3) into a group with no recurrence (5 patients) and a group (16 patients) who exhibited an 80% recurrence rate in 56 months. The separation did not reach statistical significance (p=0.096) most likely because of the small number of patients involved.

Patients who have tumors that are Gleason score 7 have a different prognosis depending on whether the tumor is Gleason grade 4+3 (worse prognosis) or Gleason grade 3+4 (better prognosis) as shown in FIG. 13. An analysis was conducted to determine if four genes that predicted a good prognosis (B3GNT5, CDC7, JUNB and KLF4) could further stratify individuals with prostate cancer with Gleason grades 3+4, (Gleason score 7) (FIG. 14) and Gleason grades 4+3 (Gleason score 7) (FIG. 15). Patients with Gleason grades 3+4 tumors could be further stratified into individuals with either a good or a worse prognosis (FIG. 14) and patients with Gleason grades 4+3 could be further stratified into those individuals with either a good or a poor (FIG. 15) prognosis.

Figure 12:
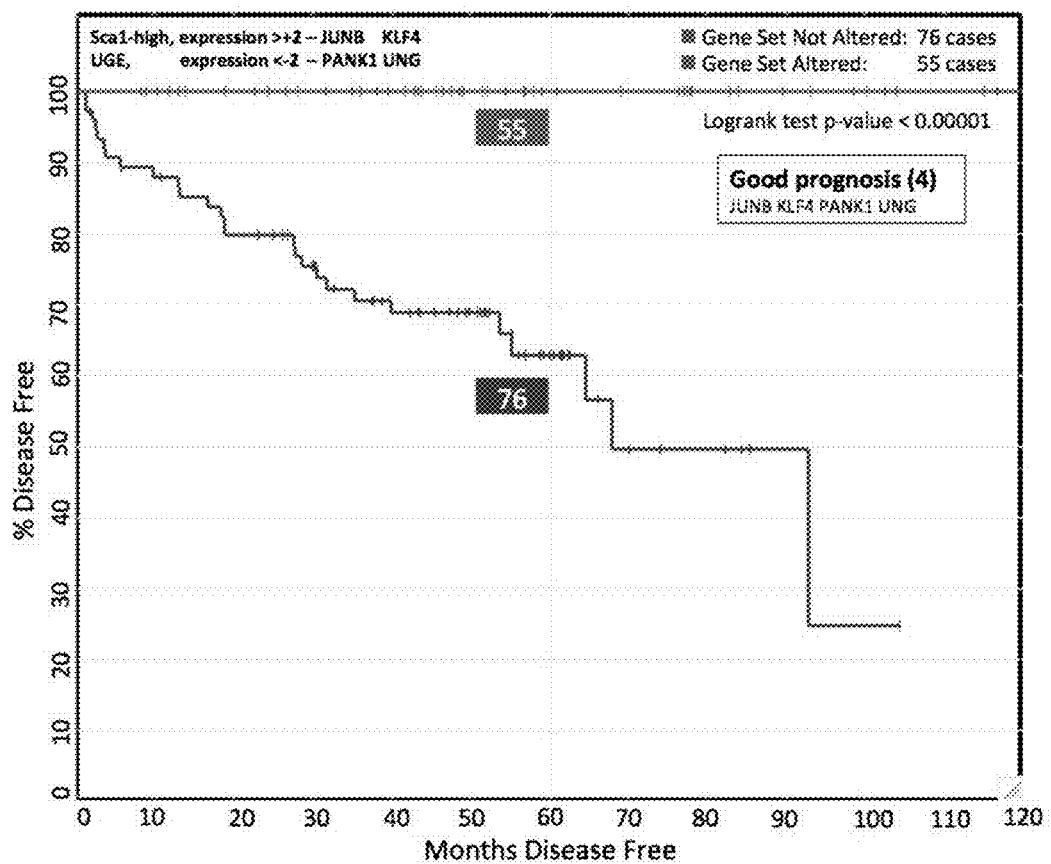
FIG. 12 is a Kaplan-Meier plot of 131 prostate cancer patients in the MSKCC database separated into two outcome groups based on the genes expressed in both the Sca 1-high (adult stem cells) and the UGE (fetal stem cells) subsets. The separation of the two groups is based on genes whose expression was significantly (p-value ≤0.05) up-regulated by a Z-score of >+2 in the Sca1-high subset and down-regulated by a Z-score of <−2 in the UGE subset in five or more patients. In this group, genes were selected such that the up-regulation in the tumor of the uniquely up-regulated Sca1-high genes, and down-regulation in the tumor of the uniquely down-regulated UGE genes indicated a significantly better disease-free survival than noted for patients whose tumors did not manifest such regulation.

An analysis was conducted to encompass all the genes in the Sca1-high (adult stem cells) and UGE subset (fetal stem cells) numbering 302 genes (represented by 641 probes) for Sca 1-high plus 953 genes (represented by 1286 probes) for UGE. Only those genes for which the separation of the Sca1-high group based on a gene expression Z-score of >+2 in five or more patients was significant as judged by a p-value less than or equal to 0.05 and for which the separation of the UGE group based on a gene expression Z-score of <−2 in five or more patients was significant as judged by a p-value less than or equal to 0.05 were considered. Four genes, JUNB, KLF4, PANK1 and UNG predicted at least 10-year biochemical relapse-free survival in roughly 42% of patients. These are the same four good prognosis genes discussed above. The Kaplan-Meier plot of the disease-free survival of patients in whose tumor cells expression of these four genes was modulated in the manner specified is shown in FIG. 12.

In light of the confirmation of predictions about use of genes expressed in adult and in fetal prostate stem cells to predict outcome of prostate cancer patients, the present invention is further drawn to the use of this concept with respect to other cancer types. As a result of the present invention, it is now expected that gene expression signatures specific to adult stem cells can be used as a predictors of outcome in other cancer types. Since most adult stem cells experience periods of proliferative quiescence, it would be expected that the same principle as found to be applicable for prostate cancer applies to breast cancer, neuronal cancer, hematopoietic cancer, and others, and serves as a predictor/prognostic measure of outcome for the cancer patients, and particularly a predictor for recurrence after surgery (or other definitive treatment), as with the prostatic data. Thus, one starts with a list of genes that are uniquely up-regulated in adult stem cells located in the tissue in which the tumor originates. Those adult stem cells are ones with a high capacity to reconstitute that particular tissue. For breast cancer, that would be the mammary gland tissue, for brain cancer, brain cells (glial and neuronal cells), for hematopoietic cancer, hematopoietic cells, etc. The unique up-regulation of such genes in the adult stem cells is as compared to fully differentiated normal cells from such tissues. Those genes, the expression of which is up-regulated as compared to the level of expression of such genes in fully differentiated cells of the same tissue, are considered to be uniquely up-regulated adult stem cell genes. The cancer patient's tumor cells are then analyzed for up-regulated expression of those uniquely up-regulated adult stem cell genes, from which it is determined that there is a good prognosis if a plurality of the uniquely up-regulated adult stem cell genes analyzed are up-regulated in the tumor cells as compared to normal tissue or tumor cells of the involved tissue from a plurality of other patients. The ability of each gene that is uniquely up-regulated in adult stem cells of the involved tissue to serve as a predictor of a good prognosis can be tested using bioinformatic analysis as discussed above with respect to prostate genes, using similar databases derived from genomic profiling of other types of cancer and following the patients' survival over a number of years. For example, the MSKCC site has prostate, colon and rectal carcinoma, ovarian carcinoma and glioblastoma, glioma, breast, head and neck squamous cell carcinoma, kidney renal cell clear carcinoma, lung adenocarcinoma, and lung squamous cell carcinoma. Other examples of known datasets useful for breast cancer include the following:

van deVijver gene set: This is a validation study of a predictive expression signature, which involves 295 young patients with early stage breast cancer, of which 151 were lymph node negative, 226 were estrogen receptor positive, and 110 had received adjuvant chemotherapy (van de Vijver et al., *N. Engl. J. Med.* 347:1999-2009 (2002)).

GSE4922: This is a derivation study for the molecular profiling of the histologic grading of breast cancer; the patients used are referred to as the Uppsala Cohort; 249 of the 316 patients in the cohort were used to derive the molecular profile of which 211 were estrogen receptor-positive, 81 were lymph node positive, and 58 showed p53 mutation. Eighty six patients which overlapped with the GSE2990 dataset were excluded, leaving 163 patients in this analysis. These data were originally published by Bergh et al., *Nature Med.* 1:1029-1034 (1995) and reinvestigated by Ivshina et al., *Cancer Res.* 66:10292-10301 (2006).

GSE2034: This is a derivation and validation analysis of a gene signature for the prediction of breast cancer patient outcomes. It consisted of 286 lymph node negative breast cancer patients who never received adjuvant chemotherapy and of which 209 were estrogen receptor positive (Wang et al., *Lancet* 365:671-679 (2005)).

GSE1456: This study is a derivation and validation analysis of a predictive gene signature for the outcomes of women with breast cancer. It involved 159 patients with breast cancer, of which 82% were estrogen receptor positive, 62% were lymph node negative and 79% were treated with adjuvant chemotherapy (Pawitan et al., Breast *Cancer Res.* 7:R953-R964 (2005)).

GSE2990: This study is a derivation and validation analysis of a correlative gene signature aimed at histologic grade. It involved 189 women with breast cancer of which 160 were lymph node negative. Sixty-four estrogen receptor positive samples were used to derive a signature that effectively differentiates outcomes and grade (Sotiriou et al., *J. Natl. Cancer Inst.* 98:262-272 (2006)).

GSE7390: This study is a multicenter validation trial, to evaluate the clinical utility of a gene signature for the management of early node negative breast cancer. The analysis involved 198 patients, of which 22 were excluded in the current analysis because of overlap with the GSE2990 dataset (Desmedt et al., *Clin. Cancer Res.* 13:3207-3214 (2007)).

Gene sets for other types of cancer are also known or may become known. Any such data set can be used for the purpose of the present invention.

A good prognosis can be determined if 1, 2, 3, 4, 5, 6, 7, 8, 9, 10, 11, 12, 13, 14, 15, 20, 25, 30 or more of the genes that are uniquely up-regulated in the adult stem cells are found to be up-regulated in the patient's tumor cells.

Similarly, in light of the present invention, it is now expected that gene expression signatures specific to fetal stem cells can be used as a predictors of outcome in other cancer types. Since most fetal stem cells have a phenotype of proliferative growth, it would be expected that the same principle as found to be applicable for prostate cancer applies to breast cancer, neuronal cancer, hematopoietic cancer, and others, and serves as a predictor/prognostic measure of outcome for the cancer patients, and particularly a predictor for recurrence after surgery (or other definitive treatment), as with the prostatic data. Thus, one starts with a list of genes that are uniquely up-regulated in fetal stem cells located in the tissue in which the tumor originates. Those fetal stem cells are ones with a high capacity to reconstitute that particular tissue. For breast cancer, that would be the mammary gland tissue, for brain cancer, brain cells (glial and neuronal cells), for hematopoietic cancer, hematopoietic cells, etc. The unique up-regulation of such genes in the fetal stem cells is as compared to fully differentiated normal cells from such tissues. Those genes the expression of which is up-regulated as compared to the level of expression of such genes in fully differentiated cells of the same tissue, are considered to be uniquely up-regulated fetal stem cell genes. The cancer patient's tumor cells are then analyzed for up-regulated expression of those uniquely up-regulated fetal stem cell genes, from which it is determined that there is a poor prognosis if a plurality of the uniquely up-regulated fetal stem cell genes analyzed are up-regulated in the tumor cells as compared to normal cells of the involved tissue or tumor cells of the involved tissue from a plurality of other patients. The ability of each gene that is uniquely up-regulated in fetal stem cells of the involved tissue to serve as a predictor of a poor prognosis can be tested using bioinformatic analysis as discussed above with respect to prostate genes, using similar databases derived from genomic profiling of other types of cancer and following the patients' survival over a number of years.

As the MSKCC prostate database is an excellent compilation of information, in which the tumor genes were consistently and rapidly analyzed from the surgically removed and rapidly frozen tumors, thereby providing a particularly accurate indication of gene activity for each such tissue sample, a bioinformatics study was undertaken to find all genes, that when modulated, i.e., have a Z-score of greater than +2 or less than −2, lead to a good or poor prognosis. The cancer genomics web portal of the Memorial Sloan Kettering Cancer Center (MSKCC) (cbio.mskcc.org/cancergenomics/prostate/data/) was accessed and data obtained by Taylor (2010), supra, consisting of the mRNA expression Z-score and clinical annotation spreadsheet files were downloaded. The data concerning the 131 patients with prostate cancer who fell into the category of "Primary Tumors with mRNA" were selected for analysis.

The goal was to find genes associated with either a good or a poor prognosis with respect to time-to-biochemical-relapse in patients who had been treated by prostatectomy for prostate cancer confined to the gland. For each gene (or gene combination), the 131 patients were separated into two groups, those with a modulated gene transcript and those without. Furthermore, the data were divided among those genes whose expression was up-regulated as compared to that of normal cells or prostate tumor cells of a plurality of other prostate tumor patients, and those whose expression was down-regulated as compared to that of normal cells or prostate tumor cells of a plurality of other prostate tumor patients. Using the survival data provided by MKSCC, and in a manner closely paralleling the analysis available though MSKCC's public portal (www.cbioportal.org/public-portal/), Kaplan-Meier curves were constructed based on the expression of various genes. Logrank tests were computed to evaluate the significance of the relative survival of patient populations whose tumors expressed different genes to yield a p-value for the impact of each gene.

To compare the impact of each gene, they were sorted in the order of the fraction of the group that had not experienced biochemical relapse at 5 years (60 months). To limit the size of the table, only those genes for which the separation of the two groups was significant with a p-value less than or equal to 0.05 were considered.

Figure 9:
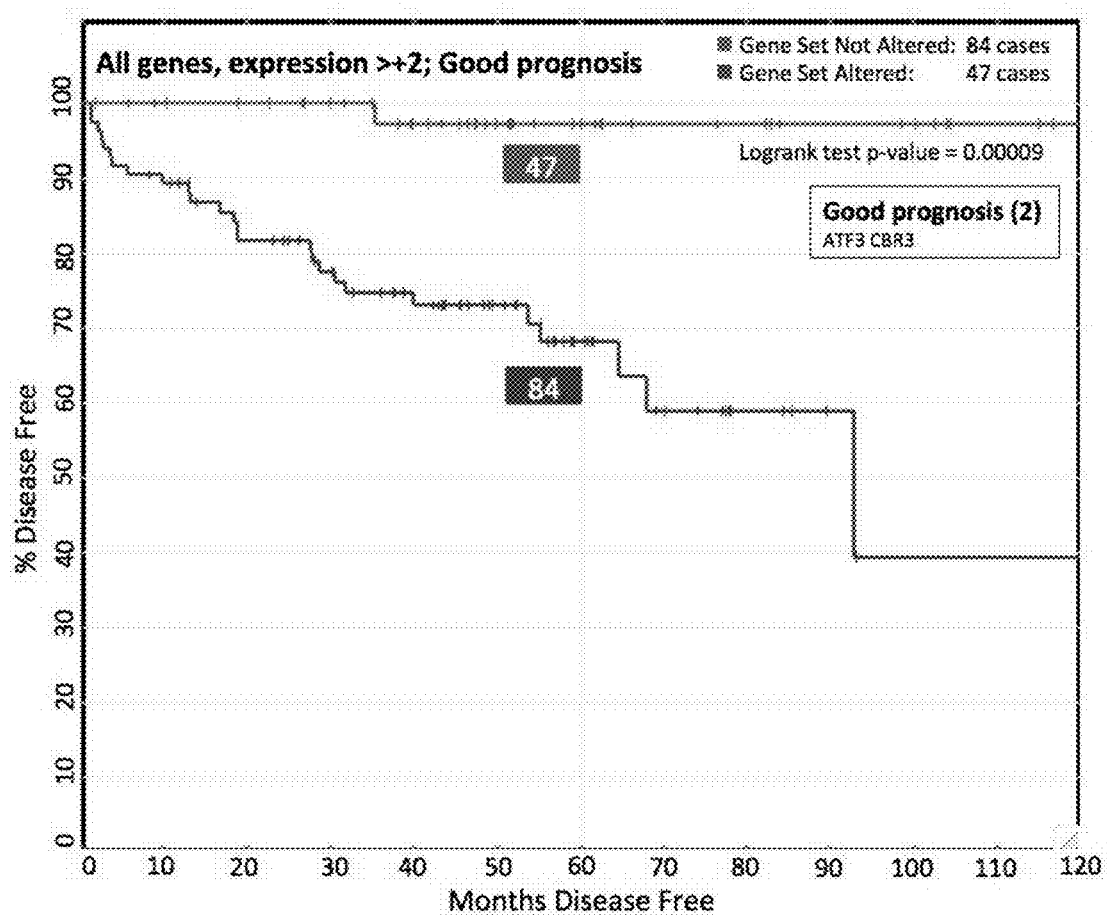
FIG. 9 is a Kaplan-Meier plot of 131 prostate cancer patients in the MSKCC database separated into two outcome groups based on all of the genes present in the microarray platform used to evaluate gene expression levels in the MSKCC tumors. The separation of the two groups is based on genes whose expression was significantly (p-value ≤0.01) up-regulated by a Z-score of >+2 in ten or more patients. In this group, genes were chosen such that their up-regulation in tumors indicated a significantly better disease-free survival than noted for patients whose tumors did not manifest such up-regulation.

Table 2 shows the results obtained when the criteria for inclusion was ten patients or more with up-regulated gene expression by a Z-score of >+2. Two genes were found that signaled a good prognosis with a p value of at least 0.01, CBR3 and ATF3. The Kaplan-Meier plot of the disease-free survival of patients in whose tumor cells the expression of these genes is up-regulated, is shown in FIG. 9.

Figure 10:
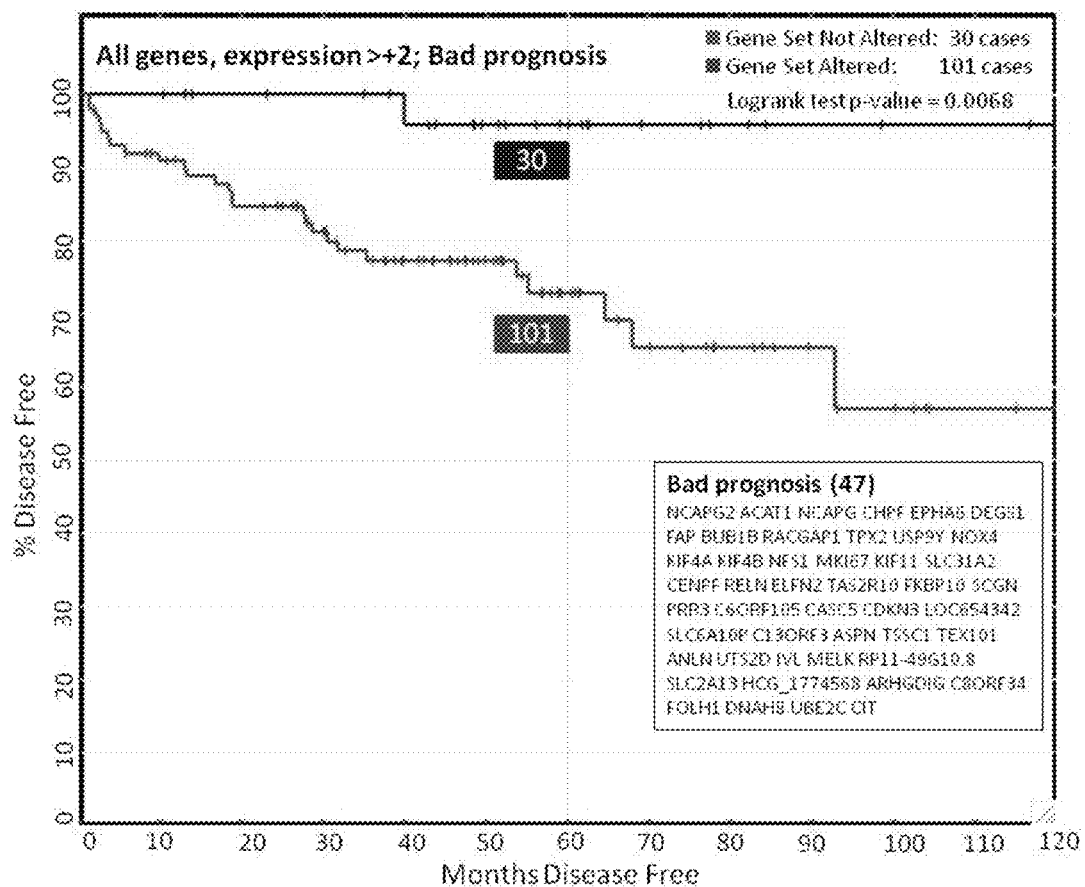
FIG. 10 is a Kaplan-Meier plot of 131 prostate cancer patients in the MSKCC database separated into two outcome groups based on all of the genes present in the microarray platform used to evaluate gene expression levels in the MSKCC tumors. The separation of the two groups is based on genes whose expression was significantly (p-value ≤0.01) up-regulated by a Z-score of >+2 in ten or more patients. In this group, genes were chosen such that their up-regulation in tumors indicated a significantly worse disease-free survival than noted for patients whose tumors did not manifest such up-regulation.

Table 2 also shows 47 genes found when the criteria for inclusion was 10 patients or more with up-regulated gene expression having a Z-score of >+2 and with a p-value of less than or equal to 0.01, in which a poor prognosis was indicated. The 47 genes found by this analysis were: ACAT1, ANLN, ARHGDIG, ASPN, BUB1B, C13ORF3, C6ORF105, C8ORF34, CASC5, CDKN3, CENPF, CHPF, CIT, DEGS1, DNAH8, ELFN2, EPHA6, FAP, FKBP10, FOLH1, HCG_1774568, IVL, KIF11, KIF4A, KIF4B, LOC654342, MELK, MKI67, NCAPG, NCAPG2, NFS1, NOX4, PRR3, RAC-GAP1, RELN, RP11-49G10.8, SCGN, SLC2A13, SLC31A2, SLC6A10P, TAS2R10, TEX101, TPX2, TSSC1, UBE2C, USP9Y, and UTS2D. The Kaplan-Meier plot of the disease-free survival of patients in whose tumor cells the expression of these genes is up-regulated is shown in FIG. 10.

Figure 11:
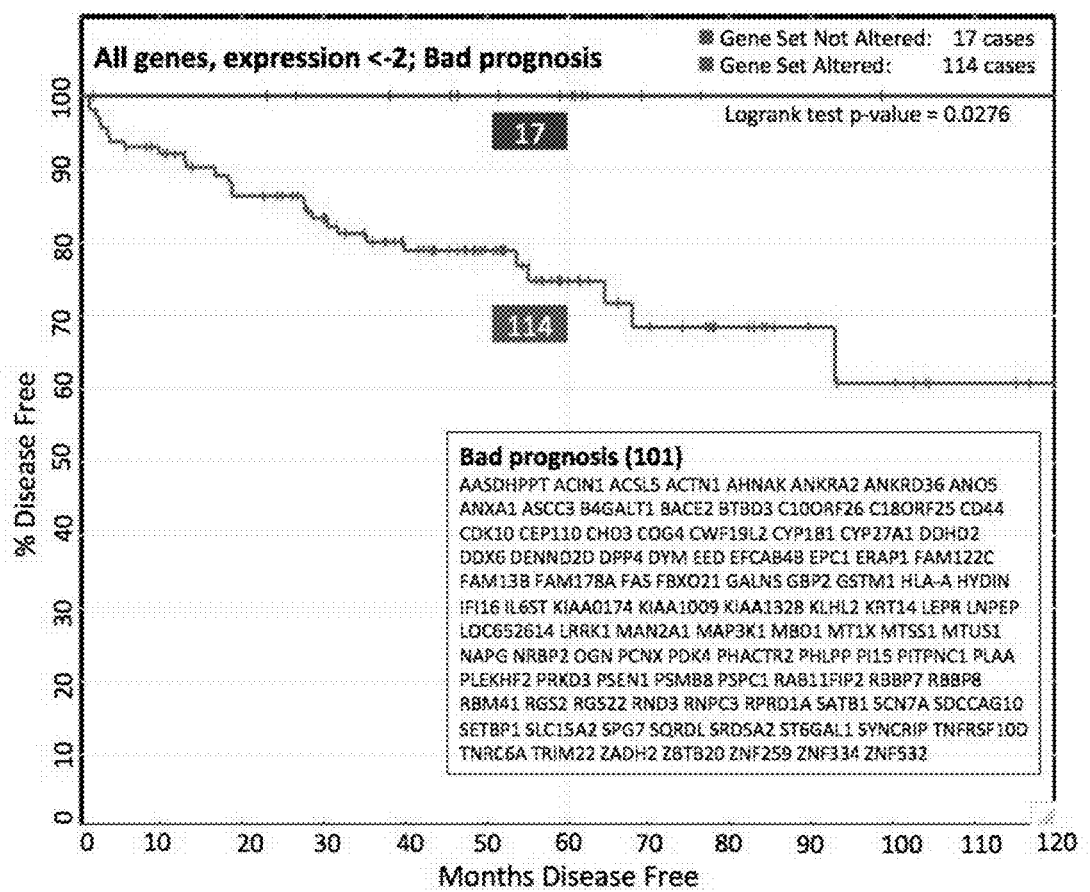
FIG. 11 is a Kaplan-Meier plot of 131 prostate cancer patients in the MSKCC database separated into two outcome groups based on all of the genes present in the microarray platform used to evaluate gene expression levels in the MSKCC tumors. The separation of the two groups is based on genes whose expression was significantly (p-value ≤0.01) down-regulated by a Z-score of <−2 in ten or more patients. In this group, genes were chosen such that their down-regulation in tumors indicated a significantly worse disease-free survival than noted for patients whose tumors did not manifest such down-regulation.

Table 1 shows the results obtained when the criteria for inclusion was ten patients or more with down-regulated gene expression represented by a Z-score of <−2. No genes were found under these selection criteria that signaled a good prognosis with a p value of less than or equal to 0.01. However, a total of 101 genes were found that signaled a poor prognosis. These were: AASDHPPT, ACIN1, ACSL5, ACTN1, AHNAK, ANKRA2, ANKRD36, ANO5, ANXA1, ASCC3, B4GALT1, BACE2, BTBD3, C10ORF26, C18ORF25, CD44, CDK10, CEP110, CHD3, COG4, CWF19L2, CYP1B1, CYP27A1, DDHD2, DDX6, DENND2D, DPP4, DYM, EED, EFCAB4B, EPC1, ERAP1, FAM122C, FAM13B, FAM178A, FAS, FBXO21, GALNS, GBP2, GSTM1, HLA-A, HYDIN, IFI16, IL6ST, KIAA0174, KIAA1009, KIAA1328, KLHL2, KRT14, LEPR, LNPEP, LOC652614, LRRK1, MAN2A1, MAP3K1, MBD1, MT1X, MTSS1, MTUS1, NAPG, NRBP2, OGN, PCNX, PDK4, PHACTR2, PHLPP, PI15, PITPNC1, PLAA, PLEKHF2, PRKD3, PSEN1, PSMB8, PSPC1, RAB11FIP2, RBBP7, RBBP8, RBM41, RGS2, RGS22, RND3, RNPC3, RPRD1A, SATB1, SCN7A, SDCCAG10, SETBP1, SLC15A2, SPG7, SQRDL, SRD5A2, ST6GAL1, SYNCRIP, TNFRSF10D, TNRC6A, TRIM22, ZADH2, ZBTB20, ZNF259, ZNF334, and ZNF532. The Kaplan-Meier plot of the disease-free survival of patients in whose tumor cells the expression of these genes was down-regulated is shown in FIG. 11.

The analysis of the tumor cells of the patient employs a molecular assay that measures expression level(s) or one or more genes, gene subsets, microRNAs, or one or more microRNAs in combination with one or more genes or gene subsets, from a biological sample obtained from the patient, and analysis of the measured expression levels to provide information concerning a good or poor prognosis. The biological sample on which the assay is run may be obtained from standard methods, including surgery, biopsy, or bodily fluids (including, but not limited to, whole blood, serum, plasma, urine, saliva, and semen) and may comprise tumor tissue or cancer cells. The protein expression products of the tumor genes may also be assayed from bodily fluids, including, but not limited to whole blood, serum, plasma, urine, saliva, and semen.

In exemplary embodiments, expression level(s) of one or more genes and/or microRNAs that are associated, positively or negatively, with a particular clinical outcome in prostate cancer are used to determine prognosis and appropriate therapy. The genes disclosed herein may be used alone or arranged in functional gene subsets, using functions such as cell proliferation or quiescence, adhesion/migration, immediate-early stress response, signaling patterns, hypoxia-induced genes, invasion, transcription factors, epigenetic modulators, association with extracellular matrix, etc. Each gene subset comprises the genes disclosed herein, as well as genes that are co-expressed with one or more of the disclosed genes. The calculation may be performed using a computer program to execute the gene expression analysis. The microRNAs disclosed herein may also be used alone or in combination with any one or more of the microRNAs and/or genes disclosed.

In exemplary embodiments, the molecular assay may involve determining expression levels of at least two genes. The genes, or gene subsets, may be weighted according to strength of association with prognosis or tumor microenvironment. In another exemplary embodiment, the molecular assay may involve expression levels of at least one gene and at least one microRNA. The gene-microRNA combination may be selected based on the likelihood that the gene-microRNA combination functionally interacts.

Techniques for assaying expression levels of gene product are discussed below.

Methods of Assaying Expression Levels of a Gene Product

The present invention employs, unless otherwise indicated, conventional techniques of molecular biology (including recombinant techniques), microbiology, cell biology, and biochemistry, which are within the skill of the art. Exemplary techniques are explained fully in the literature. See, for example: "Molecular Cloning: A Laboratory Manual", 3rd Edition (Sambrook et al., 2001); "Oligonucleotide Synthesis" (M. J. Gait, ed., 1984); "Animal Cell Culture" (R. I. Freshney, ed., 1994); "Methods in Enzymology" (Academic Press, Inc.); "Handbook of Experimental Immunology", 4th edition (D. M. Weir & C. C. Blackwell, eds., Blackwell Science Inc., 1987); "Gene Transfer Vectors for Mammalian Cells" (I. M. Miller & M. P. Calos, eds., 1987); "Current Protocols in Molecular Biology" (R. Brent et al., eds., 2003); and "PCR: The Polymerase Chain Reaction", (Mullis et al., eds., 1994).

In gene expression, the DNA constituting the gene is transcribed to form a messenger RNA (or a pre-messenger RNA that is processed, e.g., spliced to form the mature messenger RNA), and this is translated to form a polypeptide. The polypeptide itself may be subjected to post-translational processing to form a modified polypeptide, e.g., a precursor polypeptide may be subjected to cleavage to form a mature polypeptide. A protein is composed of one or more polypeptide chains and these may be covalently or non-covalently associated. A polypeptide/protein may act as a ligand, activating (or inactivating) a receptor, and thereby result in a change in the level or activity of "downstream" products mediated by that receptor. Thus, the activity (level of expression) of a gene may be detected or quantified by detecting or quantifying the corresponding messenger RNA (or a corresponding cDNA formed using that mRNA as a template), a precursor polypeptide, a mature polypeptide, or a downstream product mediated by a receptor modulated by that mature polypeptide.

Methods of gene expression profiling include methods based on hybridization analysis of polynucleotides and on sequencing of polynucleotides, and proteomics-based methods. Exemplary methods known in the art for the quantification of RNA expression in a sample include northern blotting and in situ hybridization (Parker & Barnes, *Methods in Molecular Biology* 106:247-283 (1999)); RNAse protection assays (Hod, *Biotechniques* 13:852-854 (1992)); RNAseq ("RNA-Seq: a revolutionary tool for transcriptomics," Wang, Z et al., *Nat Rev Genet*. 10(1):57-63 (2009) Review); and PCR-based methods, such as reverse transcription PCT (RT-PCR) (Weis et al., *Trends in Genetics* 8:263-264 (1992)). Antibodies may be employed that can recognize sequence specific duplexes, including DNA duplexes, RNA duplexes, and DNA-RNA hybrid duplexes or DNA-protein duplexes. Representative methods for sequencing-based gene expression analysis include Serial Analysis of Gene Expression (SAGE) and gene expression analysis by massively parallel signature sequencing (MPSS).

Reverse Transcriptase PCR (RT-PCR)

Typically, mRNA or microRNA is isolated from a test sample. The starting material is typically total RNA, e.g., isolated from a human tumor, usually from a primary tumor. Optionally, normal tissues from the same patient can be used as an internal control. Such normal tissue can be histologically-appearing normal tissue adjacent to a tumor. mRNA or microRNA can be extracted from a tissue sample that is fresh, frozen (e.g., fresh frozen), or paraffin embedded and fixed (e.g., formalin-fixed).

General methods for mRNA and microRNA extraction are well known in the art and are disclosed in standard textbooks of molecular biology, including those cited above. Methods for RNA extraction from paraffin embedded tissues are disclosed, for example, in Rupp and Locker, *Lab Invest*. 56:A67 (1987), and De Andres et al., *BioTechniques* 18:42044 (1995). In particular, RNA isolation can be performed using a purification kit, buffer set and protease from commercial manufacturers, such as Qiagen, according to the manufacturer's instructions. For example, total RNA from cells in culture can be isolated using Qiagen RNeasy mini-columns. Other commercially available RNA isolation kits include MasterPure™ Complete DNA and RNA Purification Kit (EPICENTRE®, Madison, Wis.), and Paraffin Block RNA Isolation Kit (Ambion, Inc.). Total RNA from tissue samples can be isolated using RNA Stat-60 (TelTest). RNA prepared from tumor can be isolated, for example, by cesium chloride density gradient centrifugation.

The sample containing the RNA is then subjected to reverse transcription to produce cDNA from the RNA template, followed by exponential amplification in a PCR reaction. The two most commonly used reverse transcriptases are avian myeloblastosis virus reverse transcriptase (AMV-RT) and Moloney murine leukemia virus reverse transcriptase (MoMLV-RT). The reverse transcription step is typically primed using specific primers, random hexamers, or oligo-dT primers, depending on the circumstances and the goal of expression profiling. For example, extracted RNA can be reverse-transcribed using a GeneAmp RNA PCR kit (Perkin Elmer, Calif., USA), following the manufacturer's instructions. The derived cDNA can then be used as a template in the subsequent PCR reaction.

PCR-based methods use a thermostabile DNA-dependent DNA polymerase, such as a Taq DNA polymerase. For example, TaqMan® PCR typically utilizes the 51-nuclease activity of Taq or Tth polymerase to hydrolyze a hybridization probe bound to its target amplicon, but any enzyme with equivalent 5' nuclease activity can be used. Two oligonucleotide primers are used to generate an amplicon typical of a PCR reaction product. A third oligonucleotide, or probe, can be designed to facilitate detection of a nucleotide sequence of the amplicon located between the hybridization sites the two PCR primers. The probe can be detectably labeled, e.g., with a reporter dye and can further be provided with both a fluorescent dye, and a quencher fluorescent dye, as in a Taqman® probe configuration. Where a Taqman® probe is used, during the amplification reaction, the TaqDNA polymerase enzyme cleaves the probe in a template-dependent manner. The resultant probe fragments disassociate in solution, and signal from the released reporter dye is free from the quenching effect of the second fluorophore. One molecule of reporter dye is liberated for each new molecule synthesized, and detection of the unquenched reporter dye provides the basis for quantitative interpretation of the data.

TaqMan® RT-PCR can be performed using commercially available equipment, such as, for example, high throughput platforms such as the ABI PRISM 7700 Sequence Detection System® (Perkin-Elmer-Applied Biosystems, Foster City, Calif., USA), or Lightcycler (Roche Molecular Biochemicals, Mannheim, Germany). In a preferred embodiment, the procedure is run on a LightCycler 480 (Roche Diagnostics) real-time PCR system, which is a microwell plate-based cycler platform.

5'-Nuclease assay data are commonly initially expressed as a threshold cycle ("$C_T$"). Fluorescence values are recorded during every cycle and represent the amount of product amplified to that point in the amplification reaction. The threshold cycle ($C_T$) is generally described as the point when the fluorescent signal is first recorded as statistically significant. Alternatively, data may be expressed as a crossing point ("Cp"). The Cp value is calculated by determining the second derivatives of entire qPCR amplification curves and their maximum value. The Cp value represents the cycle at which the increase of fluorescence is highest and where the logarithmic phase of a PCR begins.

To minimize errors and the effect of inter-sample variation, RT-PCR is usually performed using an internal standard. The ideal internal standard gene (also referred to as a reference gene) is expressed at a quite constant level among cancerous and non-cancerous tissue of the same origin (i.e., a level that is not significantly different among normal and cancerous tissues), and is not significantly affected by the experimental treatment (i.e., does not exhibit a significant difference in expression level in the relevant tissue as a result of exposure to chemotherapy), and expressed at a quite constant level among the same tissue taken from different patients. For example, reference genes useful in the methods disclosed herein should not exhibit significantly different expression levels in cancerous prostate as compared to normal prostate tissue. RNAs frequently used to normalize patterns of gene expression are mRNAs for the housekeeping genes glyceraldehyde-3-phosphate-dehydrogenase (GAPDH) and β-actin. Exemplary reference genes used for normalization comprise one or more of the following genes: AAMP, ARFI, ATP5E, CLTC, GPSI, and PGKI. Gene expression measurements can be normalized relative to the mean of one or more (e.g., 2, 3, 4, 5, or more) reference genes. Reference-normalized expression measurements can range from 2 to 15, where a one unit increase generally reflects a 2-fold increase in RNA quantity.

Real time PCR is compatible both with quantitative competitive PCR, where an internal competitor for each target sequence is used for normalization, and with quantitative comparative PCR using a normalization gene contained within the sample, or a housekeeping gene for RT-PCR. For further details see, e.g., Held et al., *Genome Research* 6:986-994 (1996).

The steps of a representative protocol in the present methods use fixed, paraffin-embedded tissues as the RNA source. For example, mRNA isolation, purification, primer extension and amplification can be performed according to methods available in the art (see, e.g., April C S and Fan J B, "Gene expression profiling in formalin-fixed, paraffin-embedded tissues using the whole-genome DASL assay, "*Methods Mol Biol*. 784:77-98 (2011)).

Design of PCR Primers and Probes

PCR primers and probes can be designed based upon sequences present in the mRNA transcript of the gene of interest. Primer/probe design can be performed using publicly available software, such as the DNABLAT software developed by Kent, W. J., *Genome Res*. 12(4):656-64 (2002), or by BLAST software including its variations.

Where necessary or desired, repetitive sequences of the target sequence can be masked to mitigate non-specific signals. Exemplary tools to accomplish this include the Repeat Masker program available on-line through the Baylor College of Medicine, which screens DNA sequences against a library of repetitive elements and returns a query sequence in which the repetitive elements are masked. The masked intron sequences can then be used to design primer and probe sequences using any commercially or otherwise publicly available primer/probe design packages, such as Primer Express (Applied Biosystems); MGB assay-by-design (Applied Biosystems); Primer3 (Steve Rozen and Helen J. Skaletsky (2000) Primer3 on the WWW for general users and for biologist programmers. See: S. Rrawetz, S. Misener, "Bioinformatics Methods and Protocols: Methods in Molecular Biology," pp. 365-386 (Humana Press). Other factors that can influence PCR primer design include primer length, melting temperature (Tm), and G/C content, specificity, complementary primer sequences, and 3'-end sequence. In general, optimal PCR primers are generally 17-30 bases in length, and contain about 20-80%, such as, for example, about 50-60% G+C bases, and exhibit Tm's between 50 and 80° C., e.g., about 50 to 70° C.

For further guidelines for PCR primer and probe design, see, e.g., Dieffenbach, C W et al, "General Concepts for PCR Primer Design" in: *PCR Primer, A Laboratory Manual*, Cold Spring Harbor Laboratory Press, New York, 1995, pp. 133-155; Innis and Gelfand, "Optimization of PCRs" in: *PCR Protocols, A Guide to Methods and Applications*, CRC Press, London, 1994, pp. 5-11; and Plasterer, T. N. "Primerselect: Primer and probe design" *Methods Mol. Biol*. 70: 520-527 (1997), the entire disclosures of which are hereby expressly incorporated by reference.

MassARRAY® System

In MassARRAY-based methods, such as the exemplary method developed by Sequenom, Inc. (San Diego, Calif.), following the isolation of RNA and reverse transcription, the obtained cDNA is spiked with a synthetic DNA molecule (competitor), which matches the targeted cDNA region in all positions, except a single base, and serves as an internal standard. The cDNA/competitor mixture is PCR amplified and is subjected to a post-PCR shrimp alkaline phosphatase (SAP) enzyme treatment, which results in the dephosphorylation of the remaining nucleotides. After inactivation of the alkaline phosphatase, the PCR products from the competitor and cDNA are subjected to primer extension, which generates distinct mass signals for the competitor and cDNA-derived PCR products. After purification, these products are dispensed on a chip array, which is pre-loaded with components needed for analysis with matrix-assisted laser desorption ionization time-of-flight mass spectrometry (MALDI-TOF MS) analysis. The cDNA present in the reaction is then quantified by analyzing the ratios of the peak areas in the mass spectrum generated. For further details, see, e.g., Ding and Cantor, *Proc. Nat'l. Acad. Sci. USA* 100:3059-64 (2003).

Other PCR-Based Methods

Further PCR-based techniques that can find use in the methods disclosed herein include, for example, BeadArray® technology (Illumina, San Diego, Calif.; Oliphant et al., "Discovery of Markers for Disease" (Supplement to *Biotechniques*), June 2002; Ferguson et al., *Analytical Chemistry* 72:5618 (2000)); BeadsArray for Detection of Gene Expression® (BADGE), using the commercially available Luminex100 LabMAP® system and multiple color-coded microspheres (Luminex Corp., Austin, Tex.) in a rapid assay for gene expression (Yang et al., *Genome Res.* 11:1888-98 (2001)); and high coverage expression profiling (HiCEP) analysis (Fukumura et al., *Nucl. Acids. Res.* 31(16):e94 (2003).

Proteomic Methods

Proteomic methods usually detect the polypeptide expression product of the gene. The detection reagent may be an antibody, or a specific binding fragment thereof. It may be a specific binding peptide, preferably of 5-20 aa in length. Or it may be an oligonucleotide (DNA, RNA, or an analogue thereof). Or it may be a small organic molecule (preferably under 1000 daltons) other than a peptide or oligonucleotide. In any of these cases, the peptide, oligonucleotide, or other small organic molecule may be identified by screening a suitable combinatorial library, such as those disclosed in Chang, et al. (Duke University/Karo Bio AB), EP 1,073,891.

Expression Profiling Products

The expression of an individual gene of interest may be determined (detected or quantified) by means of an affinity reagent having a specific affinity for a product correlated to the expression of that gene, such as its messenger RNA, the corresponding cDNA, the encoded polypeptide, or a downstream product of a specifically mediated receptor for said polypeptide.

If it is desirable to determine the expression of a plurality of different individual genes of interest, it may be advantageous to combine the affinity reagents for detection of the expression-correlated product into a single kit. Preferably, the methods of detection have features in common so that the kit may optionally include additional reagents or other components that would be used in practicing any of a plurality of the contemplated expression determinations. These determinations may be carried out simultaneously or sequentially.

A panel is a type of kit in which a component is provided that facilitates simultaneous determination of each of several different expression-correlated products and thus, normally, detection of quantification of expression of several different genes.

An array is a type of panel in which the affinity reagents are physically disposed on a substrate so each reagent is at a particular predefined position on the substrate. Such disposition may facilitate simultaneous synthesis of the reagents, and it also facilitates the determination of which reagents reacted positively and which negatively. One preferred array is an orthogonal grid. A microarray is an array in which the reagent quantities are small, e.g., micrograms or less.

Microarrays

Expression levels of a gene or microarray of interest can also be assessed using the microarray technique. In this method, polynucleotide sequences of interest (including cDNAs and oligonucleotides) are arrayed on a substrate. The arrayed sequences are then contacted under conditions suitable for specific hybridization with detectably labeled cDNA generated from RNA of a test sample. As in the RT-PCR method, the source of RNA typically is total RNA isolated from a tumor sample, and optionally from normal tissue of the same patient as an internal control or cell lines. RNA can be extracted, for example, from frozen or archived paraffin-embedded and fixed (e.g., formalin-fixed) tissue samples. For archived, formalin-fixed tissue cDNA-mediated annealing, selection, extension, and ligation, DASL-Illumina method may be used.

For example, PCR amplified inserts of cDNA clones of a gene to be assayed are applied to a substrate in a dense array. Usually at least 10,000 nucleotide sequences are applied to the substrate. For example, the microarrayed genes, immobilized on the microchip at 10,000 elements each, are suitable for hybridization under stringent conditions. Fluorescently labeled cDNA probes may be generated through incorporation of fluorescent nucleotides by reverse transcription of RNA extracted from tissues of interest. Labeled cDNA probes applied to the chip hybridize with specificity to each spot of DNA on the array. After washing under stringent conditions to remove non-specifically bound probes, the chip is scanned by confocal laser microscopy or by another detection method, such as a CCD camera. Quantitation of hybridization of each arrayed element allows for assessment of corresponding RNA abundance.

With dual color fluorescence, separately labeled cDNA probes generated from two sources of RNA are hybridized pair wise to the array. The relative abundance of the transcripts from the two sources corresponding to each specified gene is thus determined simultaneously. The miniaturized scale of the hybridization affords a convenient and rapid evaluation of the expression pattern for large numbers of genes. Such methods have been shown to detect rare transcripts, which are expressed at a few copies per cell, and to reproducibly detect at least approximately two-fold differences in the expression levels (Schena et at, *Proc. Natl. Acad. Sci USA* 93(2):106-49 (1996)). Microarray analysis can be performed by commercially available equipment, following manufacturer's protocols, such as by using the Affymetrix GenChip® technology, or Incyte's microarray technology.

Focused Microarray Analysis

Protocols with an integrated platform for studying relative transcript expression, including microarray design and fabrication, analysis and calibration algorithms, and high throughput quantitative real-time PCR, are known and any such protocol can be used with the present invention. In this regard, the following publication is hereby incorporated herein by reference: Wurmbaugh et al, "Focused microarray analysis," *Methods* 31:306-316 (2003).

Serial Analysis of Gene Expression (SAGE)

Serial analysis of gene expression (SAGE) is a method that allows the simultaneous and quantitative analysis of a large number of gene transcripts, without the need of providing an individual hybridization probe for each transcript. First, a short sequence tag (about 10-14 bp) is generated that contains sufficient information to uniquely identify a transcript, provided that the tag is obtained from a unique position within each transcript. Then, many transcripts are linked together to form long serial molecules, that can be sequenced, revealing the identity of the multiple tags simultaneously. The expression pattern of any population of transcripts can be quantitatively evaluated by determining the abundance of individual tags, and identifying the gene corresponding to each tag. For more details see, e.g., Velculescu et al., *Science* 270:484-7 (1995); and Velculescu et al., *Cell* 88:243-51 (1997).

Gene Expression Analysis by Nucleic Acid Sequencing

Nucleic acid sequencing technologies are suitable methods for analysis of gene expression. The principle underlying these methods is that the number of times a cDNA sequence is detected in a sample is directly related to the relative expression of the RNA corresponding to that sequence. These methods are sometimes referred to by the term Digital Gene Expression (DGE) to reflect the discrete numeric property of the resulting data. Early methods applying this principle were Serial Analysis of Gene Expression (SAGE) and Massively Parallel Signature Sequencing (MPSS). See, e.g., S. Brenner, et al., *Nature Biotechnology* 18(6):630-34 (2000). More recently, the advent of "next-generation" sequencing technologies has made DGE simpler, higher throughput, and more affordable. As a result, more laboratories are able to utilize DGE to screen the expression of more genes in more individual patient samples than previously possible. See, e.g., J. Marioni, *Genome Research* 18(9):1509-17 (2008); R. Morin, *Genome Research* 18(4):610-21 (2008); A. Mortazavi, *Nature Methods* 5(7):621-28 (2008); N. Cloonan, *Nature Methods* 5(7):613-19 (2008).

RNA-Seq

RNA-Seq uses recently developed deep-sequencing technologies. In general, a population of RNA (total or fractionated, such as poly(A)+) is converted to a library of cDNA fragments with adaptors attached to one or both ends. Each molecule, with or without amplification, is then sequenced in a high-throughput manner to obtain short sequences from one end (single-end sequencing) or both ends (pair-end sequencing). The reads are typically 30-400 bp, depending on the DNA-sequencing technology used. In principle, any high-throughput sequencing technology25 can be used for RNA-Seq. Following sequencing, the resulting reads are either aligned to a reference genome or reference transcripts, or assembled de novo without the genomic sequence to produce a genome-scale transcription map that consists of both the transcriptional structure and/or level of expression for each gene. To avoid artifacts and biases generated by reverse transcription direct RNA sequencing can also be applied. Ozsolak and Milos, "Single-molecule direct RNA sequencing without cDNA synthesis," *Nature Review Genetics* 12:87-98 (2011).

Aptamer-Based Multiplexed Proteomic Technology

Aptamer-based proteomic technology can be used for biomarker measurement. This technique allows simultaneous measurement of thousands of proteins from small sample volumes. This technique is described, for example, in Gold et al, "Aptamer-Based Multiplexed Proteomic Technology for Biomarker Discovery," *PLoS ONE* 5(12):e15004. doi: 10.1371/journal.pone.0015004 (2010) and Ostroff et al. "Early Detection of Malignant Pleural Mesothelioma in Asbestos-Exposed Individuals with a Noninvasive Proteomics-Based Surveillance Tool," *PLoS ONE* 7(10): e46091. doi: 10.1371/journal.pone.0046091 (2012), both of which are hereby incorporated herein by reference.

Isolating RNA from Body Fluids

Methods of isolating RNA for expression analysis from blood, plasma and serum (see, e.g., K. Enders, et al., *Clin Chem* 48:1647-53 (2002) (and references cited therein) and from urine (see, e.g., R. Boom, et al., *J Clin Microbiol.* 28: 495-503 (1990) and references cited therein) have been described.

Immunohistochemistry

Immunohistochemistry methods are also suitable for detecting the expression levels of genes and applied to the method disclosed herein. Antibodies (e.g., monoclonal antibodies) that specifically bind a gene product of a gene of interest can be used in such methods. The antibodies can be detected by direct labeling of the antibodies themselves, for example, with radioactive labels, fluorescent labels, hapten' labels such as, biotin, or an enzyme such as horseradish peroxidase or alkaline phosphatase. Alternatively, unlabeled primary antibody can be used in conjunction with a labeled secondary antibody specific for the primary antibody. Immunohistochemistry protocols and kits are well known in the art and are commercially available.

Proteomics

The term "proteome" is defined as the totality of the proteins present in a sample (e.g., tissue, organism, or cell culture) at a certain point of time. Proteomics includes, among other things, study of the global changes of protein expression in a sample (also referred to as "expression proteomics"). Proteomics typically includes the following steps: (1) separation of individual proteins in a sample by 2-D gel electrophoresis (2-D PAGE); (2) identification of the individual proteins recovered from the gel, e.g., by mass spectrometry or N-terminal sequencing, and (3) analysis of the data using bioinformatics.

General Description of the mRNA/microRNA Isolation, Purification and Amplification The steps of a representative protocol for profiling gene expression using either fixed, paraffin-embedded tissues (for archival studies) or using frozen samples (for prospective studies) as the RNA source, including mRNA or microRNA isolation, purification, primer extension and amplification are provided in various publications. (See, e.g., T. E. Godfrey, et al., *J. Molec. Diagnostics* 2:84-91 (2000); K. Specht et al., *Am. J. Pathol.* 158:419-29 (2001), M. Cronin, et al., *Am J Pathol* 164:35-42 (2004)). Briefly, a representative process starts with cutting a tissue sample section (e.g., about 10 μm thick sections of a paraffin-embedded tumor tissue sample). The RNA is then extracted, and protein and DNA are removed. After analysis of the RNA concentration, RNA repair is performed if desired. The sample can then be subjected to analysis, e.g., by reverse transcription using gene specific promoters followed by RT-PCR.

Normalization of Expression Levels

The expression data used in the methods disclosed herein can be normalized. Normalization refers to a process to correct for (or normalize), for example, differences in the amount of RNA assayed and variability in the quality of the RNA used, to remove unwanted sources of systematic variation in $C_T$ or Cp measurements, and the like. With respect to RT-PCR experiments involving archived fixed paraffin embedded tissue samples, sources of systematic variation are known to include the degree of RNA degradation relative to the age of the patient sample and the type of fixative used to store the sample. Other sources of systematic variation are attributable to laboratory processing conditions. More recent tumor banking involves frozen samples of tumor and normal tissue. Normalization is also useful to correct for systematic variation.

Assays can provide normalization by incorporating the expression of certain normalizing genes, which do not differ significantly in expression levels under the relevant conditions. Exemplary normalization genes include housekeeping genes. (See, e.g., E. Eisenberg, et al., *Trends in Genetics* 19(7):362-65 (2003).) Normalization can be based on the mean or median signal ($C_T$ or Cp) of all of the assayed genes or a large subset thereof (global normalization approach). In general, the normalizing genes, also referred to as reference genes should be genes that are known not to exhibit significantly different expression in prostate cancer as compared to non-cancerous prostate tissue, and are not significantly affected by various sample and process conditions, thus providing for normalizing away extraneous effects.

In exemplary embodiments, one or more of the following genes may be used as references by which the mRNA or microRNA expression data is normalized: AAMP, ARFI, ATP5E, CLTC, GPSI, and PGKI. In another exemplary embodiment, one or more of the following microRNAs may be used as references by which the expression data of microRNAs are normalized: hsa-miR-106a; hsa-miR-146b-5p; -hsa-miR-191; hsa-miR-19b; and hsa-miR-92a. The calibrated weighted average $C_T$ or Cp measurements for each of the prognostic and predictive genes or microRNAs may be normalized relative to the mean of five or more reference genes or microRNAs.

Those skilled in the art will recognize that normalization may be achieved in numerous ways, and the techniques described above are intended only to be exemplary, not exhaustive.

Standardization of Expression Levels

The expression data used in the methods disclosed herein can be standardized. Standardization refers to a process to effectively put all the genes or microRNAs on a comparable scale. This is performed because some genes or microRNAs will exhibit more variation (a broader range of expression) than others. Standardization is performed by dividing each expression value by its standard deviation across all samples for that gene or microRNA. Hazard ratios are then interpreted as the relative risk of recurrence per 1 standard deviation increase in expression.

The present invention is also directed to kits that may be used for practicing any of the methods of the present invention. Such kits will include a set of affinity reagents that will specifically detect expression of the specific genes, the expression levels of which are used in the analysis of the methods of the present invention. The affinity reagents are preferably arranged on a microarray. Preferably, the microarray used is one created for use with the methods of the present invention and include only affinity reagents for detecting gene or protein expression of the genes discussed herein, along with a number of control genes, such as housekeeping genes, for use in normalization of the results. Preferably, the microarray would contain no more than about 25, 20, 15, or 10 affinity reagents for control genes or protein products expressed thereby. A microarray for use in the kit of the present invention preferably includes fewer than 2,501 affinity reagents, more preferably fewer than 626, most preferably fewer than 101. Preferably, such a microarray includes affinity reagents specific for no more than 10,000, 5,000, 4,000 or 3,000 total affinity reagents.

The kits in accordance with the present invention may include any of the material, reagents, software, etc., that is disclosed in any of the publications incorporated by reference hereinabove for practicing various known methods of gene or protein expression analysis.

EXAMPLE 1

Figure 16:
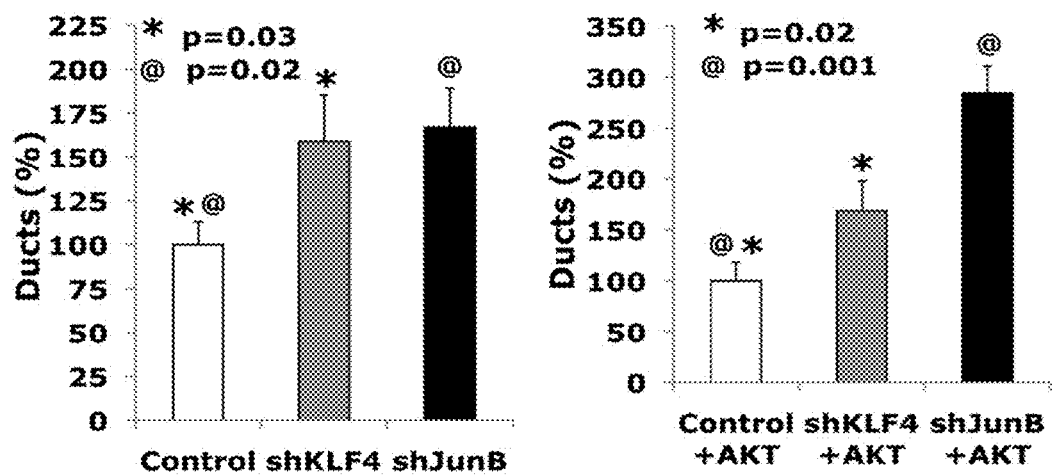
FIG. 16 is a bar graph showing the increase in duct formation (indicative of stem cell self-renewal) in primary murine prostate cells (control) and in primary murine prostate cells in which KLF4 or JunB has been knocked down (shKLF4 or shJunB). Primary murine proximal prostate cells were infected with shRNA-lentivirus knockdown (KD) constructs alone (left panel) or together with activated AKT (right panel). KD resulted in significantly more ducts in collagen gels as compared to control.

KLF4 and JUNB Inhibit Growth and Impede Transformation of Primitive Primary Murine Prostate Cells Compared to non-stem cells, adult prostate stem cells (APSCs) express 29-fold more KLF4 and 5-fold more JUNB, both predictors of good prognosis. ShRNA-lentivirus knockdown (KD) of KLF4 or JUNB in primary proximal cells reduced KLF4 by 91%, and JUNB by 80%. Reduction in the expression of these two genes increased stem cell number and their self-renewal as determined by the percent of cells that formed ducts in 3D-collagen gels (FIG. 16, left panel), their size (1.8- and 3.1-fold for KLF4 and JUNB KD, respectively), and their ability to reconstitute sub-renal capsule (RC) prostate tissue (1.4 fold, p<0.03 and 2.3 fold, p<0.04 for KLF4 and JUNB KD, respectively). These effects were even more pronounced when KLF4 or JUNB were knocked down and the cells were simultaneously transformed by co-infection with RFP-active-AKT-expressing lenti-constructs (FIG. 16, right panel), a pathway active in the majority of prostate cancers. Specifically, the AKT/KLF4 KD duct size increased 3-fold and AKT/JUNB KD 11.7-fold. In addition, AKT/KLF4 KD in primary cells produced larger sub-RC tumors than control AKT transformed cells (0.6 g±0.1 vs 0.4 g±0.1, p<0.02), and the tumors were frank adenocarcinomas rather than the mainly PIN lesions found in AKT with intact KLF4 suggesting that KLF4 impedes AKT-induced transformation. Both sub-RC KLF4 KD tissue (2.2-fold) and AKT/KLF4 KD tumors (2.9-fold) had more basal cells than the controls, suggesting that KLF4 affects stem cell homeostasis. AKT/JUNB KD in primary cells also resulted in larger sub-RC tumors than control AKT transformed cells (1.0 g±0.3 vs 0.6 g±0.2, p=0.01). These data indicate that KLF4 and JUNB inhibit the proliferation of normal primitive prostate cells and that they also antagonize oncogenic transformation mediated by activated AKT, thereby confirming their applicability as a diagnostic biomarker of quiescence in prostate cancer, as described herein.

EXAMPLE 2

KLF4 and JUNB Inhibit Growth and Impede Transformation of Stable Murine and Human Prostate Cell Lines To establish cell lines to be used as models for testing the role of KLF4 and JUNB, a stable cell line was isolated from a tumor derived from murine Sca-1$^{high}$ stem cells that had been transformed by AKT. Stable AKT/KLF4 KD, AKT/JUNB KD and control cell lines were then generated by infecting cells with sh-lentivirus (reduction of the target genes 87-95%). KLF4 KD (76% reduction) and control lines were also generated using a murine prostate stem cell line, WFU (Barclay et al. "Characterization of adult prostatic progenitor/stem cells exhibiting self-renewal and multilineage differentiation," *Stem Cells* 26(3):600-610 (2008); Barclay and Cramer. "Culture of mouse prostatic epithelial cells from genetically engineered mice," *Prostate* 63(3):291-298 (2005)).

In addition, stable KLF4 KD (83% reduction) was generated in a human prostate stem cell line, WPE (Tokar et al. "Stem/progenitor and intermediate cell types and the origin of human prostate cancer," *Differentiation* 73(9-10):463-473 (2005); Xu et al. "Arsenic-Transformed Malignant Prostate Epithelia Can Convert Noncontiguous Normal Stem Cells into an Oncogenic Phenotype," *Environ Health Perspect* 120 (6):865-71 (2012)).

Figure 17:
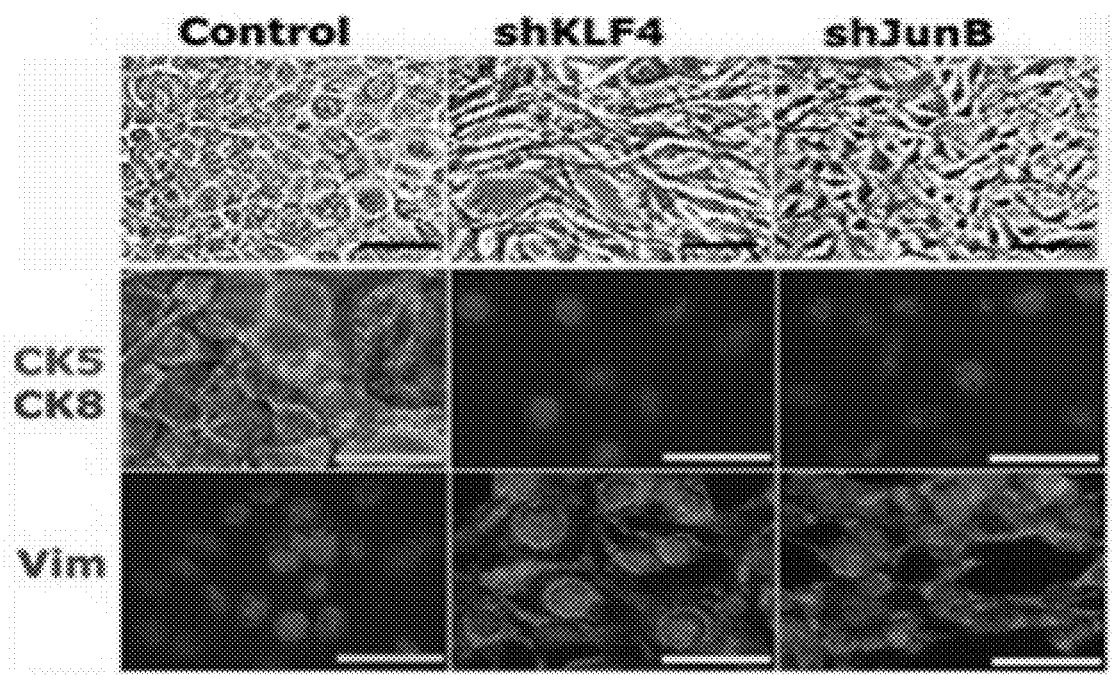
FIG. 17 shows a series of microphotographs for cells of a murine Sca-1$^{high}$ AKT tumor derived prostate cell line (Control), that cell line infected with shRNA-lentivirus knockdown (KD) with KLF4 constructs (shKLF4) and that cell line infected with shRNA-lentivirus knockdown (KD) with JunB constructs (shJunB). In the top row of microphotographs, the pronounced epithelial-mesenchymal transition (EMT) morphology in KLF4 KD cells (shKLF4) and JunB KD cells (shJunB) is shown. The second row of microphotographs shows that KD inhibited CK5 (green) and CK8 (red) protein expression. The third row of microphotographs shows that KD increased vimentin (Vim-red) protein expression. The scale bar is equal to 50 µm.
Figure 18:
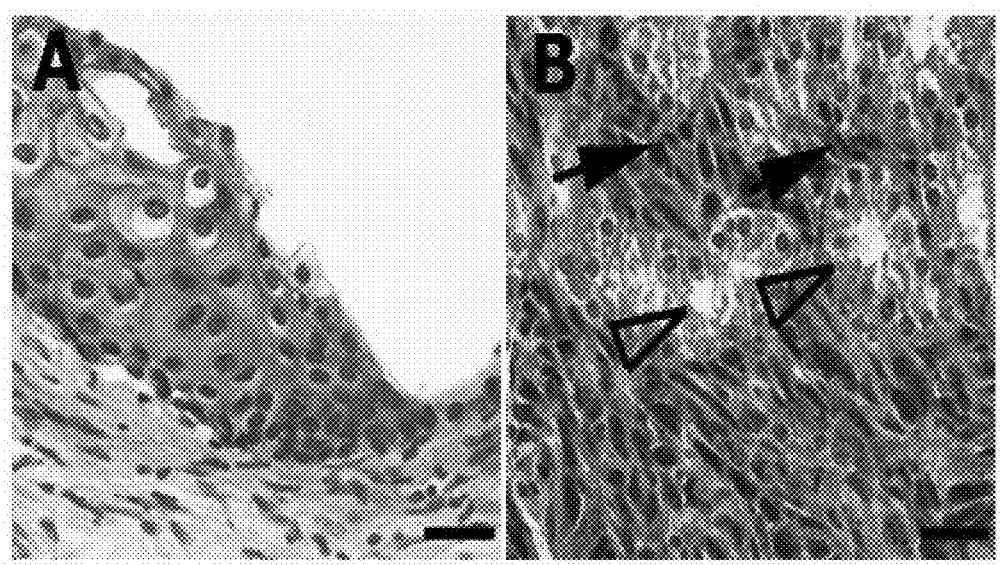
FIG. 18 depicts microphotographs showing that KLF4 knockdown (KD) in cells of a murine Sca-1$^{high}$ AKT tumor derived prostate cell line results in invasive sarcomatoid carcinomas.

KD of KLF4 and JUNB in the murine Sca-1$^{high}$ AKT tumor derived cell line resulted in a 4-6-fold increase in growth and a concurrent pronounced epithelial-mesenchymal transition (EMT) evidenced by morphology, decreased CKs, increased vimentin (FIG. 17) and decreased E-cadherin protein (not shown). Profound EMT-compatible changes in gene expression and in tumor initiating cell (TIC) content (in Matrigel) were found (Table 7). TICs had 53% and 68% lower levels of KLF4 and JUNB protein, respectively, than the cells from which they originated. The increase in TIC numbers in the AKT/KLF4 KD and AKT/JUNB KD cell lines coincided with rapid growth (~1.5 g in 4 weeks) of invasive sarcomatoid carcinomas while the AKT control cell line formed only small PIN lesions sub-RC (FIG. 18), indicating that reduction in KLF4 and JUNB promotes EMT in vitro and enhances tumorigenicity of the AKT cell line in vivo.

In the human prostate WPE stem cell line, KD of KLF4 (83% reduction in protein) increased growth in culture by 2-3 fold, increased prostatospheres in Matrigel by 5-fold and further shifted the percent of basal cells from an already high 65% in control to 95% in the KLF 4KD cells (p=0.006). Thus, in the WPE human stem cell line, as with the murine cell lines tested, KLF4 KD favors proliferation and promotes a less differentiated basal phenotype.

This experiment also further supports the concept that these genes may serve as a diagnostic biomarker of quiescence in prostate cancer, as described herein.

TABLE 1

| Gene | Logrank | p-value | # Altered | # Unaltered | Relapse-free survival |
|---|---|---|---|---|---|
| SPG7 | 9.43733 | 0.0021 | 42 | 89 | Short |
| SRD5A2 | 10.7539 | 0.001 | 39 | 92 | Short |
| HYDIN | 11.6196 | 0.0007 | 19 | 112 | Short |
| CYP27A1 | 15.2899 | 0.0001 | 42 | 89 | Short |
| KRT14 | 9.9639 | 0.0016 | 25 | 106 | Short |
| ACTN1 | 10.7818 | 0.001 | 38 | 93 | Short |
| LRRK1 | 9.48556 | 0.0021 | 19 | 112 | Short |
| TRIM22 | 10.9997 | 0.0009 | 33 | 98 | Short |
| CHD3 | 12.3193 | 0.0004 | 17 | 114 | Short |
| ZNF532 | 12.7775 | 0.0004 | 30 | 101 | Short |
| TNFRSF10D | 11.5906 | 0.0007 | 21 | 110 | Short |
| GSTM1 | 10.031 | 0.0015 | 25 | 106 | Short |
| ZNF259 | 15.0567 | 0.0001 | 26 | 105 | Short |
| ZBTB20 | 10.8121 | 0.001 | 25 | 106 | Short |
| RBBP8 | 9.45392 | 0.0021 | 22 | 109 | Short |
| KLHL2 | 9.62352 | 0.0019 | 22 | 109 | Short |
| RGS2 | 9.97476 | 0.0016 | 22 | 109 | Short |
| GBP2 | 13.1108 | 0.0003 | 24 | 107 | Short |
| RGS22 | 11.2097 | 0.0008 | 19 | 112 | Short |
| C10ORF26 | 15.665 | 0.0001 | 20 | 111 | Short |
| RND3 | 11.9007 | 0.0006 | 20 | 111 | Short |
| CD44 | 10.745 | 0.001 | 17 | 114 | Short |
| LOC652614 | 10.2963 | 0.0013 | 15 | 116 | Short |
| ANO5 | 10.3564 | 0.0013 | 17 | 114 | Short |
| CDK10 | 13.3423 | 0.0003 | 16 | 115 | Short |
| ZNF334 | 9.8981 | 0.0017 | 15 | 116 | Short |
| AHNAK | 12.4427 | 0.0004 | 12 | 119 | Short |
| EED | 10.3155 | 0.0013 | 17 | 114 | Short |
| HLA-A | 12.9067 | 0.0003 | 16 | 115 | Short |
| PI15 | 16.95 | 0 | 23 | 108 | Short |
| RBBP7 | 9.74963 | 0.0018 | 14 | 117 | Short |
| NRBP2 | 12.8851 | 0.0003 | 11 | 120 | Short |
| ST6GAL1 | 10.0584 | 0.0015 | 15 | 116 | Short |
| KIAA1328 | 10.9099 | 0.001 | 15 | 116 | Short |
| KIAA1009 | 9.74781 | 0.0018 | 17 | 114 | Short |
| ASCC3 | 10.6874 | 0.0011 | 13 | 118 | Short |
| RAB11FIP2 | 10.5983 | 0.0011 | 15 | 116 | Short |
| SATB1 | 10.2236 | 0.0014 | 13 | 118 | Short |
| ERAP1 | 13.0589 | 0.0003 | 21 | 110 | Short |
| PITPNC1 | 9.88967 | 0.0017 | 18 | 113 | Short |
| ACIN1 | 16.5521 | 0 | 15 | 116 | Short |
| PSMB8 | 17.4122 | 0 | 19 | 112 | Short |
| PSPC1 | 14.0082 | 0.0002 | 11 | 120 | Short |
| PLAA | 9.67942 | 0.0019 | 12 | 119 | Short |
| MTSS1 | 14.1844 | 0.0002 | 18 | 113 | Short |
| FAM178A | 10.8843 | 0.001 | 12 | 119 | Short |
| DDX6 | 12.0592 | 0.0005 | 11 | 120 | Short |
| PSEN1 | 10.0559 | 0.0015 | 11 | 120 | Short |
| MT1X | 11.0525 | 0.0009 | 11 | 120 | Short |
| ANKRD36 | 14.6764 | 0.0001 | 15 | 116 | Short |
| MTUS1 | 11.206 | 0.0008 | 10 | 121 | Short |
| DPP4 | 10.409 | 0.0013 | 11 | 120 | Short |
| MBD1 | 19.5824 | 0 | 15 | 116 | Short |
| IFI16 | 14.7952 | 0.0001 | 13 | 118 | Short |
| MAP3K1 | 12.7227 | 0.0004 | 13 | 118 | Short |
| EPC1 | 14.5609 | 0.0001 | 14 | 117 | Short |
| SLC15A2 | 13.1193 | 0.0003 | 15 | 116 | Short |
| PDK4 | 12.0283 | 0.0005 | 11 | 120 | Short |

TABLE 1-continued

| Gene | Logrank | p-value | # Altered | # Unaltered | Relapse-free survival |
|---|---|---|---|---|---|
| CEP110 | 11.852 | 0.0006 | 16 | 115 | Short |
| B4GALT1 | 13.3284 | 0.0003 | 11 | 120 | Short |
| FAM122C | 12.2204 | 0.0005 | 11 | 120 | Short |
| PRKD3 | 10.9469 | 0.0009 | 17 | 114 | Short |
| FAM13B | 9.49085 | 0.0021 | 13 | 118 | Short |
| PHLPP | 10.9656 | 0.0009 | 12 | 119 | Short |
| RPRD1A | 11.4674 | 0.0007 | 10 | 121 | Short |
| DENND2D | 13.9144 | 0.0002 | 10 | 121 | Short |
| ZADH2 | 17.1609 | 0 | 15 | 116 | Short |
| SYNCRIP | 10.8598 | 0.001 | 11 | 120 | Short |
| RNPC3 | 11.7252 | 0.0006 | 10 | 121 | Short |
| SQRDL | 15.0602 | 0.0001 | 13 | 118 | Short |
| LEPR | 12.0843 | 0.0005 | 10 | 121 | Short |
| EFCAB4B | 24.1311 | 0 | 12 | 119 | Short |
| FBXO21 | 11.9534 | 0.0005 | 10 | 121 | Short |
| PCNX | 11.0704 | 0.0009 | 13 | 118 | Short |
| BACE2 | 9.55496 | 0.002 | 10 | 121 | Short |
| ANKRA2 | 10.0516 | 0.0015 | 11 | 120 | Short |
| CWF19L2 | 14.6937 | 0.0001 | 11 | 120 | Short |
| MAN2A1 | 11.5343 | 0.0007 | 12 | 119 | Short |
| DYM | 14.9873 | 0.0001 | 10 | 121 | Short |
| SDCCAG10 | 14.3609 | 0.0002 | 13 | 118 | Short |
| BTBD3 | 18.3008 | 0 | 11 | 120 | Short |
| KIAA0174 | 17.4591 | 0 | 13 | 118 | Short |
| ANXA1 | 21.6372 | 0 | 12 | 119 | Short |
| RBM41 | 15.4845 | 0.0001 | 10 | 121 | Short |
| GALNS | 18.9765 | 0 | 10 | 121 | Short |
| AASDHPPT | 18.5028 | 0 | 10 | 121 | Short |
| COG4 | 15.5157 | 0.0001 | 10 | 121 | Short |
| SETBP1 | 11.167 | 0.0008 | 10 | 121 | Short |
| PHACTR2 | 15.9521 | 0.0001 | 12 | 119 | Short |
| PLEKHF2 | 16.9216 | 0 | 10 | 121 | Short |
| FAS | 16.4549 | 0 | 11 | 120 | Short |
| IL6ST | 14.4563 | 0.0001 | 12 | 119 | Short |
| DDHD2 | 17.0901 | 0 | 11 | 120 | Short |
| LNPEP | 11.7564 | 0.0006 | 10 | 121 | Short |
| ACSL5 | 11.8783 | 0.0006 | 11 | 120 | Short |
| C18ORF25 | 20.2398 | 0 | 12 | 119 | Short |
| CYP1B1 | 16.7638 | 0 | 12 | 119 | Short |
| NAPG | 11.3972 | 0.0007 | 10 | 121 | Short |
| TNRC6A | 19.6413 | 0 | 10 | 121 | Short |
| OGN | 32.9651 | 0 | 18 | 113 | Short |
| SCN7A | 35.3227 | 0 | 10 | 121 | Short |

TABLE 2

| Gene | Logrank | p-value | # Altered | # Unaltered | Relapse-free survival |
|---|---|---|---|---|---|
| CBR3 | 8.198 | 0.0042 | 27 | 104 | Long |
| ATF3 | 7.453 | 0.0063 | 30 | 101 | Long |
| NCAPG2 | 9.628 | 0.0019 | 30 | 101 | Short |
| ACAT1 | 10.024 | 0.0015 | 10 | 121 | Short |
| NCAPG | 12.754 | 0.0004 | 25 | 106 | Short |
| CHPF | 12.552 | 0.0004 | 17 | 114 | Short |
| EPHA6 | 10.676 | 0.0011 | 21 | 110 | Short |
| DEGS1 | 10.519 | 0.0012 | 19 | 112 | Short |
| FAP | 12.579 | 0.0004 | 16 | 115 | Short |
| BUB1B | 12.136 | 0.0005 | 19 | 112 | Short |
| RACGAP1 | 11.127 | 0.0009 | 17 | 114 | Short |
| TPX2 | 15.078 | 0.0001 | 24 | 107 | Short |
| USP9Y | 11.296 | 0.0008 | 10 | 121 | Short |
| NOX4 | 17.798 | 0 | 21 | 110 | Short |
| KIF4A | 14.423 | 0.0001 | 18 | 113 | Short |
| KIF4B | 14.423 | 0.0001 | 18 | 113 | Short |
| NFS1 | 10.549 | 0.0012 | 13 | 118 | Short |

TABLE 2-continued

| Gene | Logrank | p-value | # Altered | # Unaltered | Relapse-free survival |
|---|---|---|---|---|---|
| MKI67 | 18.315 | 0 | 19 | 112 | Short |
| KIF11 | 9.5 | 0.0021 | 33 | 98 | Short |
| SLC31A2 | 13.263 | 0.0003 | 13 | 118 | Short |
| CENPF | 17.285 | 0 | 18 | 113 | Short |
| RELN | 13.489 | 0.0002 | 18 | 113 | Short |
| ELFN2 | 11.468 | 0.0007 | 14 | 117 | Short |
| TAS2R10 | 10.702 | 0.0011 | 11 | 120 | Short |
| FKBP10 | 12.924 | 0.0003 | 10 | 121 | Short |
| SCGN | 15.767 | 0.0001 | 13 | 118 | Short |
| PRR3 | 11.497 | 0.0007 | 15 | 116 | Short |
| C6ORF105 | 12.451 | 0.0004 | 16 | 115 | Short |
| CASC5 | 10.963 | 0.0009 | 11 | 120 | Short |
| CDKN3 | 12.255 | 0.0005 | 17 | 114 | Short |
| LOC654342 | 12.213 | 0.0005 | 12 | 119 | Short |
| SLC6A10P | 10.88 | 0.001 | 11 | 120 | Short |
| C13ORF3 | 15.65 | 0.0001 | 15 | 116 | Short |
| ASPN | 19.269 | 0 | 12 | 119 | Short |
| TSSC1 | 15.248 | 0.0001 | 14 | 117 | Short |
| TEX101 | 10.531 | 0.0012 | 11 | 120 | Short |
| ANLN | 14.901 | 0.0001 | 13 | 118 | Short |
| UTS2D | 13.795 | 0.0002 | 11 | 120 | Short |
| IVL | 10.185 | 0.0014 | 11 | 120 | Short |
| MELK | 19.088 | 0 | 17 | 114 | Short |
| RP11-49G10.8 | 11.351 | 0.0008 | 10 | 121 | Short |
| SLC2A13 | 10.316 | 0.0013 | 10 | 121 | Short |
| HCG_1774568 | 10.749 | 0.001 | 13 | 118 | Short |
| ARHGDIG | 15.144 | 0.0001 | 13 | 118 | Short |
| C8ORF34 | 14.348 | 0.0002 | 15 | 116 | Short |
| FOLH1 | 27.99 | 0 | 10 | 121 | Short |
| DNAH8 | 15.3 | 0.0001 | 11 | 120 | Short |
| UBE2C | 22.218 | 0 | 12 | 119 | Short |
| CIT | 26.477 | 0 | 11 | 120 | Short |

TABLE 3

Sca 1-high, expression > +2 Total probe number altered in Sca 1-high subset - 641

| Gene | Logrank | p-value | # altered | # un-altered | Prognosis |
|---|---|---|---|---|---|
| KLF4 | 6.38412 | 0.0115 | 21 | 110 | Good |
| JUNB | 4.09768 | 0.0430 | 14 | 117 | Good |
| PTPRR | 17.3402 | 0.0000 | 9 | 122 | Poor |
| SYT9 | 14.2585 | 0.0002 | 9 | 122 | Poor |
| DUSP26 | 12.1405 | 0.0005 | 5 | 126 | Poor |
| IVL | 10.1847 | 0.0014 | 11 | 120 | Poor |
| RAMP2 | 9.93969 | 0.0016 | 12 | 119 | Poor |
| WNT4 | 9.42031 | 0.0021 | 6 | 125 | Poor |
| THSD1 | 8.91885 | 0.0028 | 11 | 120 | Poor |

TABLE 4

Sca 1-high, expression < −2

| Gene | Logrank | p-val | # altered | # unaltered | Prognosis |
|---|---|---|---|---|---|
| CASP4 | 24.6659 | 0.0000 | 8 | 123 | Poor |
| CTR9 | 22.3933 | 0.0000 | 6 | 125 | Poor |
| LEPR | 12.0843 | 0.0005 | 10 | 121 | Poor |
| SH3RF2 | 11.9884 | 0.0005 | 6 | 125 | Poor |

TABLE 5

UGE, expression > +2 Total probe number altered in UGE subset - 1286

| Gene | Logrank | p-value | # altered | # unaltered | Prognosis |
|---|---|---|---|---|---|
| CDC7 | 4.20286 | 0.0404 | 17 | 114 | Good |
| B3GNT5 | 3.90485 | 0.0481 | 15 | 116 | Good |
| UBE2C | 22.2183 | 0.0000 | 12 | 119 | Poor |
| CIT | 26.477 | 0.0000 | 11 | 120 | Poor |
| IRS4 | 30.4466 | 0.0000 | 7 | 124 | Poor |
| MELK | 19.0884 | 0.0000 | 17 | 114 | Poor |
| MKI67 | 18.3153 | 0.0000 | 19 | 112 | Poor |
| NOX4 | 17.7982 | 0.0000 | 21 | 110 | Poor |
| PTPRR | 17.3402 | 0.0000 | 9 | 122 | Poor |
| CENPF | 17.2849 | 0.0000 | 18 | 113 | Poor |
| TPX2 | 15.0781 | 0.0001 | 24 | 107 | Poor |
| KIF4A | 14.4228 | 0.0001 | 18 | 113 | Poor |
| KIF4B | 14.4228 | 0.0001 | 18 | 113 | Poor |
| SYT9 | 14.2585 | 0.0002 | 9 | 122 | Poor |
| NCAPG | 12.7544 | 0.0004 | 25 | 106 | Poor |
| CDKN3 | 12.2553 | 0.0005 | 17 | 114 | Poor |
| EME1 | 12.1405 | 0.0005 | 5 | 126 | Poor |
| KRT1 | 12.1405 | 0.0005 | 5 | 126 | Poor |
| BUB1B | 12.1356 | 0.0005 | 19 | 112 | Poor |
| SLC35F1 | 11.7995 | 0.0006 | 6 | 125 | Poor |
| RACGAP1 | 11.1272 | 0.0009 | 17 | 114 | Poor |
| ESPL1 | 11.0728 | 0.0009 | 5 | 126 | Poor |
| CASC5 | 10.9631 | 0.0009 | 11 | 120 | Poor |
| CCNA2 | 10.2096 | 0.0014 | 7 | 124 | Poor |
| IVL | 10.1847 | 0.0014 | 11 | 120 | Poor |
| NCAPG2 | 9.62804 | 0.0019 | 30 | 101 | Poor |
| MLF1IP | 9.57339 | 0.0020 | 15 | 116 | Poor |
| KIF11 | 9.50049 | 0.0021 | 33 | 98 | Poor |
| UNC13C | 9.48373 | 0.0021 | 7 | 124 | Poor |
| WNT4 | 9.42031 | 0.0021 | 6 | 125 | Poor |
| DLGAP5 | 9.33542 | 0.0022 | 18 | 113 | Poor |
| INCENP | 9.26365 | 0.0023 | 8 | 123 | Poor |
| PSAT1 | 9.17189 | 0.0025 | 13 | 118 | Poor |
| THSD1 | 8.91885 | 0.0028 | 11 | 120 | Poor |
| E2F8 | 8.87663 | 0.0029 | 6 | 125 | Poor |
| IGF2BP3 | 8.72612 | 0.0031 | 5 | 126 | Poor |
| BRCA1 | 8.41627 | 0.0037 | 8 | 123 | Poor |
| PRC1 | 8.31396 | 0.0039 | 41 | 90 | Poor |
| BNC1 | 8.12543 | 0.0044 | 5 | 126 | Poor |
| HBE1 | 8.12543 | 0.0044 | 5 | 126 | Poor |
| NUSAP1 | 8.01947 | 0.0046 | 20 | 111 | Poor |
| EVPL | 7.9276 | 0.0049 | 6 | 125 | Poor |
| ONECUT2 | 7.9205 | 0.0049 | 24 | 107 | Poor |
| EFNA3 | 7.89415 | 0.0050 | 6 | 125 | Poor |
| PSAPL1 | 7.75066 | 0.0054 | 5 | 126 | Poor |
| DIRAS2 | 7.6243 | 0.0058 | 6 | 125 | Poor |
| CENPI | 7.50769 | 0.0061 | 20 | 111 | Poor |
| WT1 | 7.50155 | 0.0062 | 5 | 126 | Poor |
| TTK | 7.4643 | 0.0063 | 20 | 111 | Poor |
| ZFP41 | 7.44767 | 0.0064 | 10 | 121 | Poor |
| SMC2 | 7.12949 | 0.0076 | 7 | 124 | Poor |

TABLE 6

UGE, expression < −2

| Gene | Logrank | p-value | # altered | # unaltered | Prognosis |
|---|---|---|---|---|---|
| PANK1 | 8.42773 | 0.0037 | 28 | 103 | Good |
| UNG | 3.99404 | 0.0457 | 13 | 118 | Good |

TABLE 7

Effect of KLF4 or JUNB KD on EMT genes and TICs

|  | KD KLF4/Cont | KD JUNB/Cont |
|---|---|---|
| E-cad (Q-PCR) | 74% | 60% |
| N-cad (Q-PCR) | 78-fold | 290-fold |

TABLE 7-continued

Effect of KLF4 or JUNB KD on EMT genes and TICs

|  | KD KLF4/Cont | KD JUNB/Cont |
| --- | --- | --- |
| SLUG (Q-PCR) | Not changed | 5-fold |
| TIC (spheres) | 8.8-fold | 13.5-fold |

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

We claim:

1. A kit for determining expression of at least seven genes selected from the group consisting of JUNB, KLF4, FOXH1, FOS, CLDN4, PADI4, B3GNT5, CDC7, PANK1, UNG, CBR3, and ATF3, comprising:
    a set of affinity reagents to specifically detect expression of said at least seven genes, wherein said set of affinity reagents contains fewer than 2,501 affinity reagents; and
    a substrate on which each of said affinity reagents are physically immobilized at a particular predefined position.

2. The kit of claim 1, further comprising at least one signal producing system that, used in conjunction with at least one of said affinity reagents, generates a signal if said affinity reagent binds to a marker of expression of the gene for which said reagent is specific, the presence of said signal indicating expression of said gene or the level of said signal correlating to the level of expression of said gene.

3. A kit in accordance with claim 1, wherein said set of affinity reagents further includes affinity reagents to detect expression of control genes.

4. A kit in accordance with claim 1, for detecting all of the genes JUNB, KLF4, FOXH1, FOS, CLDN4, PADI4, B3GNT5, CDC7, PANK1, UNG, CBR3, and ATF3, wherein said set of affinity reagents specifically detect expression of all twelve of said genes.

5. A kit in accordance with claim 1, wherein said affinity reagents specifically detect protein expression products of said genes.

6. A kit in accordance with claim 1, wherein said affinity reagents specifically detect RNA transcription from said genes.

7. A kit in accordance with claim 1, wherein said set of affinity reagents are chosen so as to specifically detect expression of at least nine of said group of genes.

8. A kit in accordance with claim 1, wherein said set of affinity reagents contains fewer than 101 affinity reagents.

9. A kit for determining expression of at least six genes selected from the group consisting of JUNB, KLF4, FOXH1, FOS, CLDN4, PADI4, B3GNT5, CDC7, PANK1, UNG, CBR3, and ATF3, comprising:
    a set of affinity reagents to specifically detect expression of said at least six genes, wherein said set of affinity reagents contains fewer than 626 affinity reagents; and
    a substrate on which each of said affinity reagents are physically immobilized at a particular predefined position.

10. The kit of claim 9, further comprising at least one signal producing system that, used in conjunction with at least one of said affinity reagents, generates a signal if said affinity reagent binds to a marker of expression of the gene for which said reagent is specific, the presence of said signal indicating expression of said gene or the level of said signal correlating to the level of expression of said gene.

11. A kit in accordance with claim 9, wherein said set of affinity reagents contains fewer than 101 affinity reagents.

12. A kit in accordance with claim 9, wherein said set of affinity reagents further includes affinity reagents to detect expression of control genes.

13. A kit in accordance with claim 9, for detecting all of the genes JUNB, KLF4, FOXH1, FOS, CLDN4, PADI4, B3GNT5, CDC7, PANK1, UNG, CBR3, and ATF3, wherein said set of affinity reagents specifically detect expression of all twelve of said genes.

14. A kit in accordance with claim 9, wherein said affinity reagents specifically detect protein expression products of said genes.

15. A kit in accordance with claim 9, wherein said affinity reagents specifically detect RNA transcription from said genes.

16. A kit in accordance with claim 9, wherein said set of affinity reagents are chosen so as to specifically detect expression of at least seven of said group of genes.

17. A kit for determining expression of at least seven genes selected from the group consisting of JUNB, KLF4, FOXH1, FOS, CLDN4, PADI4, B3GNT5, CDC7, PANK1, UNG, CBR3, and ATF3, comprising:
    a set of affinity reagents to specifically detect expression of said at least seven genes, wherein said set of affinity reagents contains fewer than 2,501 affinity reagents; and
    at least one signal producing label attached directly or indirectly to the affinity reagent, said signal producing label being selected from the group consisting of a radioactive, enzymatic, hapten, reporter dye or fluorescent label.

18. A kit in accordance with claim 17, wherein said set of affinity reagents further includes affinity reagents to detect expression of control genes.

19. A kit in accordance with claim 17, for detecting all of the genes JUNB, KLF4, FOXH1, FOS, CLDN4, PADI4, B3GNT5, CDC7, PANK1, UNG, CBR3, and ATF3, wherein said set of affinity reagents specifically detect expression of all twelve of said genes.

20. A kit in accordance with claim 17, wherein said set of affinity reagents are chosen so as to specifically detect expression of at least nine of said group of genes.

21. A kit in accordance with claim 17, wherein said set of affinity reagents contains fewer than 101 affinity reagents.

22. A kit in accordance with claim 17, wherein said affinity reagents specifically detect protein expression products of said genes.

23. A kit in accordance with claim 17, wherein said affinity reagents specifically detect RNA transcription from said genes.

24. A kit for determining expression of at least six genes selected from the group consisting of JUNB, KLF4, FOXH1, FOS, CLDN4, PADI4, B3GNT5, CDC7, PANK1, UNG, CBR3, and ATF3, comprising:
    a set of affinity reagents to specifically detect expression of said at least six genes, wherein said set of affinity reagents contains fewer than 626 affinity reagents; and
    at least one signal producing label attached directly or indirectly to the affinity reagent, said signal producing label being selected from the group consisting of a radioactive, enzymatic, hapten, reporter dye or fluorescent label.

25. A kit in accordance with claim 24, wherein said set of affinity reagents further includes affinity reagents to detect expression of control genes.

26. A kit in accordance with claim 24, for detecting all of the genes JUNB, KLF4, FOXH1, FOS, CLDN4, PADI4, B3GNT5, CDC7, PANK1, UNG, CBR3, and ATF3, wherein said set of affinity reagents specifically detect expression of all twelve of said genes.

27. A kit in accordance with claim 24, wherein said affinity reagents specifically detect protein expression products of said genes.

28. A kit in accordance with claim 24, wherein said set of affinity reagents are chosen so as to specifically detect expression of at least seven of said group of genes.

29. A kit in accordance with claim 24, wherein said set of affinity reagents are chosen so as to specifically detect expression of at least nine of said group of genes.

30. A kit in accordance with claim 24, wherein said set of affinity reagents contains fewer than 101 affinity reagents.

31. A kit in accordance with claim 24, wherein said affinity reagents specifically detect RNA transcription from said genes.

* * * * *